(12) United States Patent
Kametani

(10) Patent No.: US 10,482,897 B2
(45) Date of Patent: Nov. 19, 2019

(54) BIOLOGICAL SOUND ANALYZING APPARATUS, BIOLOGICAL SOUND ANALYZING METHOD, COMPUTER PROGRAM, AND RECORDING MEDIUM

(71) Applicant: PIONEER CORPORATION, Bunkyo-ku, Tokyo (JP)

(72) Inventor: Ryushin Kametani, Kawagoe (JP)

(73) Assignee: PIONEER CORPORATION, Tokyo (JP)

( * ) Notice: Subject to any disclaimer, the term of this patent is extended or adjusted under 35 U.S.C. 154(b) by 0 days.

(21) Appl. No.: 16/073,312

(22) PCT Filed: Jan. 29, 2016

(86) PCT No.: PCT/JP2016/052835
§ 371 (c)(1),
(2) Date: Jul. 26, 2018

(87) PCT Pub. No.: WO2017/130417
PCT Pub. Date: Aug. 3, 2017

(65) Prior Publication Data
US 2019/0051315 A1 Feb. 14, 2019

(51) Int. Cl.
*G10L 15/00* (2013.01)
*G10L 21/0264* (2013.01)
(Continued)

(52) U.S. Cl.
CPC ............ *G10L 21/0264* (2013.01); *A61B 5/08* (2013.01); *A61B 7/04* (2013.01); *G06F 17/141* (2013.01);
(Continued)

(58) Field of Classification Search
CPC combination set(s) only.
See application file for complete search history.

(56) References Cited

U.S. PATENT DOCUMENTS

2013/0328683 A1* 12/2013 Sitbon ..................... G06F 19/00
340/573.6

FOREIGN PATENT DOCUMENTS

| JP | 2004-357758 A | 12/2004 |
|---|---|---|
| JP | 2005-066045 A | 3/2005 |
| JP | 2014-028111 A | 2/2014 |
| JP | 2014-050672 A | 3/2014 |

OTHER PUBLICATIONS

International Search Report for related International Application No. PCT/JP2016/052825, dated Apr. 26, 2016; English translation provided; 4 pages.
(Continued)

*Primary Examiner* — Vu B Hang
(74) *Attorney, Agent, or Firm* — Procopio, Cory, Hargreaves & Savitch LLP

(57) ABSTRACT

A biological sound analyzing apparatus is provided with: an obtaining device configured to obtain first biological sound information, which indicates a change in biological sounds with time; a processing device configured to generate second biological sound information by performing a first process of enhancing first noise information, which indicates noise included in the biological sounds, on the first biological sound information; a calculating device configured to calculate correlation information, which indicates a correlation in adjacent periods of the second biological sound information; and an outputting device configured to output second noise information, which indicates continuous noise included in the biological sounds, on the basis of the correlation coefficient. This makes it possible to analyze continuous noise included in the obtained biological sounds.

17 Claims, 19 Drawing Sheets

(51) Int. Cl.
*G10L 15/20* (2006.01)
*A61B 7/04* (2006.01)
*A61B 5/08* (2006.01)
*G06F 17/15* (2006.01)
*G10L 25/06* (2013.01)
*G10L 25/66* (2013.01)
*G06F 17/14* (2006.01)
G10L 25/24 (2013.01)
G10L 21/00 (2013.01)

(52) U.S. Cl.
CPC ............ *G06F 17/156* (2013.01); *G10L 15/20* (2013.01); *G10L 25/06* (2013.01); *G10L 25/66* (2013.01); *G10L 21/00* (2013.01); *G10L 25/24* (2013.01)

(56) References Cited

OTHER PUBLICATIONS

Fuchida et al., "Detection Algorithm for Continuous Adventitious Lung Sounds", Yakuri to Rinsho, Sep. 2007, pp. 481-487; vol. 17, No. 5; English abstract provided.
Suzuki, Akifumi "Development of a Lung-sound Monitor for the Real-time Detection of Adventitious Sounds", Yakuri to Rinsho, Sep. 2009, pp. 365-369; vol. 19, No. 5; English abstract provided.
Waida et al., "Sounds feature extraction for breath state detection algorithm", Report of the Meeting, the Acoustical Society of Japan, edited by The Acoustical Society of Japan (ASJ), Mar. 3, 2014, pp. 805-808.

\* cited by examiner

Rhonchi tendency
calculation section

BIOLOGICAL SOUND ANALYZING APPARATUS, BIOLOGICAL SOUND ANALYZING METHOD, COMPUTER PROGRAM, AND RECORDING MEDIUM

CROSS-REFERENCE TO RELATED APPLICATIONS

This application is a U.S. National Stage entry of PCT Application No: PCT/JP2016/052835 filed Jan. 29, 2016, the contents of which are incorporated herein by reference.

TECHNICAL FIELD

The present invention relates to a biological sound analyzing apparatus and a biological sound analyzing method for analyzing biological sounds, which may include noise, such as, for example, continuous adventitious lung sounds, a computer program, and a recording medium.

BACKGROUND ART

For this type of apparatus, there is known an apparatus configured to detect adventitious sounds, i.e., sounds that are different from normal breath sounds, wherein the adventitious sounds are included in breath sounds of a living body detected by an electronic stethoscope or the like. For example, Patent Literature 1 discloses a technology/technique in which an amplitude spectrum, a phase spectrum, and a power spectrum are calculated by a Fast Fourier Transform (FFT) process and in which the normal breath sounds and the continuous sounds are distinguished by determining whether or not a local variance value of the power spectrum exceeds a threshold value. Moreover, Patent Literature 2 discloses a technology/technique in which a peak that can be determined to be erroneously detected is removed after the detection of a peak position on an autocorrelation function, to thereby detect the continuous sounds.

CITATION LIST

Patent Literature

Patent Literature 1: Japanese Patent Application Laid Open No. 2004-357758
Patent Literature 2: Japanese Patent Application Laid Open No. 2014-28111

SUMMARY OF INVENTION

Technical Problem

In the technologies/techniques described in the Patent Literatures 1 and 2 described above, after the FFT process is performed, the peak of the spectrum is used to detect the continuous sounds. In the continuous sounds, however, the peak does not appear equally due to individual differences and an influence of a measurement environment or the like. Thus, if the continuous sounds are detected only from the peak, detection accuracy is reduced. In the technologies/techniques described in the Patent Literatures 1 and 2, the continuous sounds included in the biological sounds cannot be accurately detected, which is technically problematic.

An example of problems to be solved by the present invention includes the aforementioned technical problem. It is therefore an object of the present invention to provide a biological sound analyzing apparatus and a biological sound analyzing method in which the noise included in the biological sounds can be preferably analyzed, a computer program, and a recording medium.

Solution to Problem

The above object of the present invention can be achieved by a biological sound analyzing apparatus provided with: an obtaining device configured to obtain first biological sound information, which indicates a change in biological sounds with time; a processing device configured to generate second biological sound information by performing a first process of enhancing first noise information, which indicates noise included in the biological sounds, on the first biological sound information; a calculating device configured to calculate correlation information, which indicates a correlation in adjacent periods of the second biological sound information; and an outputting device configured to output second noise information, which indicates continuous noise included in the biological sounds, on the basis of the correlation information.

The above object of the present invention can be achieved by a biological sound analyzing method provided with: an obtaining process of obtaining first biological sound information, which indicates a change in biological sounds with time; a processing process of generating second biological sound information by performing a first process of enhancing first noise information, which indicates noise included in the biological sounds, on the first biological sound information; a calculating process of calculating correlation information, which indicates a correlation in adjacent periods of the second biological sound information; and an outputting process of outputting second noise information, which indicates continuous noise included in the biological sounds, on the basis of the correlation information.

The above object of the present invention can be achieved by a computer program product for making a computer perform: an obtaining process of obtaining first biological sound information, which indicates a change in biological sounds with time; a processing process of generating second biological sound information by performing a first process of enhancing first noise information, which indicates noise included in the biological sounds, on the first biological sound information; a calculating process of calculating correlation information, which indicates a correlation in adjacent periods of the second biological sound information; and an outputting process of outputting second noise information, which indicates continuous noise included in the biological sounds, on the basis of the correlation information.

The above object of the present invention can be achieved by a recording medium on which the computer program product described above is recorded.

DESCRIPTION OF EMBODIMENTS

<1>

Figure 1:
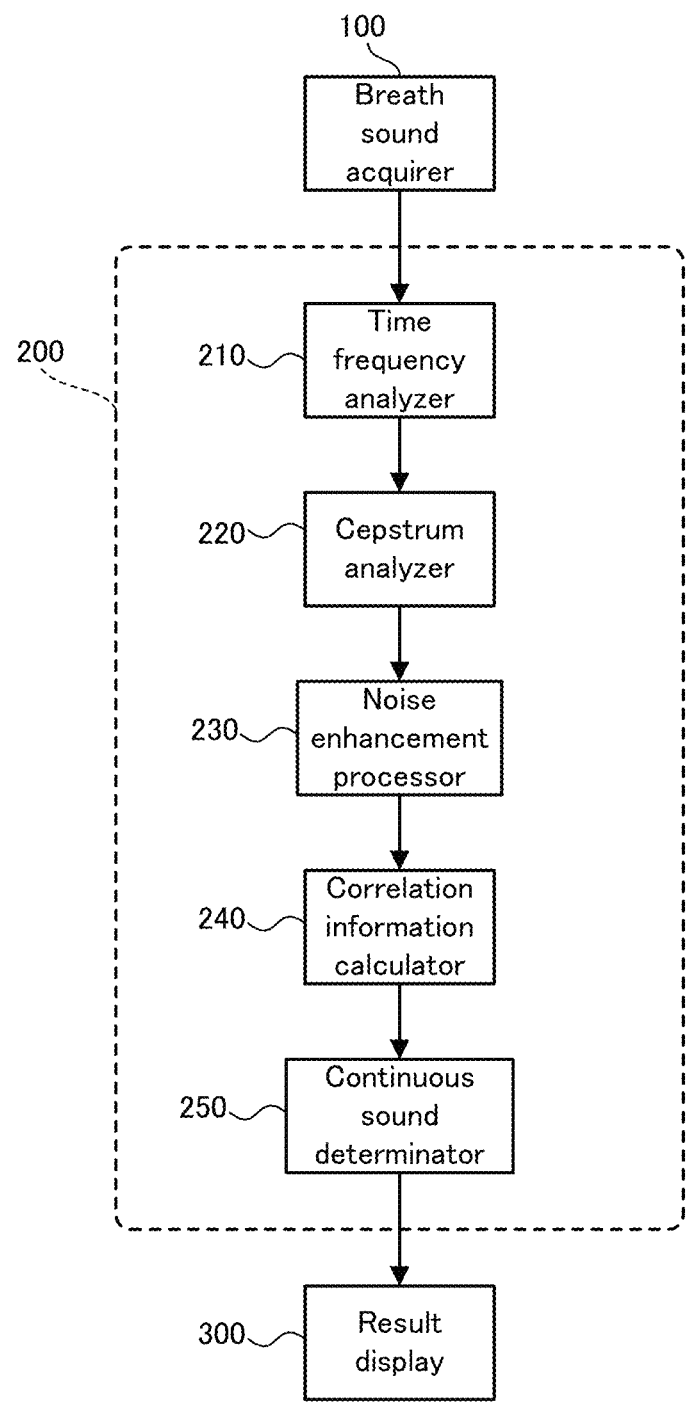
FIG. 1 is a block diagram illustrating a configuration of a biological sound analyzing apparatus according to an example.

A biological sound analyzing apparatus according to an embodiment is provided with: an obtaining device configured to obtain first biological sound information, which indicates a change in biological sounds with time; a processing device configured to generate second biological sound information by performing a first process of enhancing first noise information, which indicates noise included in the biological sounds, on the first biological sound information; a calculating device configured to calculate correlation information, which indicates a correlation in adjacent periods of the second biological sound information; and an outputting device configured to output second noise information, which indicates continuous noise included in the biological sounds, on the basis of the correlation information.

According to the biological sound analyzing apparatus in the embodiment, in operation thereof, the first biological sound information is firstly obtained by the obtaining device. The "biological sounds" may be sounds generated by a living body, and are typically breath sounds. Moreover, the "first biological sound information" may be information that indicates the change in the biological sounds with time, and may be obtained, for example, as a time-axis waveform indicating the biological sounds.

If the first biological sound information is obtained, the first process is performed on the first biological sound information by the processing device. The first process is a process of enhancing the first noise information, which indicates the noise included in the biological sounds. The "noise" may be abnormal sounds that are not included in normal biological sounds (e.g., adventitious sounds included in breath sounds, etc). The first noise information may be, for example, information indicating the presence or absence of the noise, information indicating the type of the noise, the intensity of the noise, or the like.

As the first process, the existing process, such as, for example, a cepstral mean normalization (CMN) process and a liftering process (which is specifically a process of cutting a low-degree quefrency component of a cepstrum) can be used. By performing the first process, the second biological sound information in which the first noise information is enhanced in comparison with the first biological sound is generated.

If the second biological sound information is generated, the correlation information of the second biological sound information is calculated by the calculating device. The "correlation information" herein may be information indicating the correlation in the adjacent periods of the second biological sound information. The correlation information can be calculated, for example, as a correlation coefficient of cepstrum information between adjacent frames out of a plurality of frames into which the second biological information is divided. In this case, as the correlation between the adjacent frames is stronger, the correlation information (or the correlation coefficient) is calculated to have a larger value.

If the correlation information is calculated, the second noise information, which indicates the continuous noise included in the biological sounds (e.g., continuous sounds, etc.), is outputted by the outputting device. Particularly in the embodiment, the second noise information is outputted on the basis of the aforementioned correlation information. Specifically, a sound in which the correlation information is large, i.e., in which the correlation in the adjacent periods is strong, is determined to be the continuous noise, and the second noise information is outputted in accordance with the determination result.

The continuous noise indicated by the second noise information appears temporally continuously on a spectrogram due to its characteristics. Thus, it can be considered that the correlation in the adjacent periods is also strong in comparison with another sound (e.g., discontinuous sounds, etc.). Thus, if the continuous noise is determined or distinguished on the basis of the correlation information, it is possible to output more accurate second noise information in view of temporal continuity.

<2>

In one aspect of the biological sound analyzing apparatus according to the embodiment, the processing device is configured to calculate power spectrum information by performing a Fourier transform process on the first biological sound information, and is configured to perform a process of reducing a component that is less than or equal to a predetermined degree, from cepstrum information, which is calculated by taking a logarithm of the power spectrum information and performing an inverse Fourier transform process, as the first process.

According to this aspect, a so-called liftering process is performed as the first process. In the liftering process, the component that is less than or equal to the predetermined degree is reduced from the ceptstrum information, by which a characteristic part of the noise can be emphasized. It is thus possible to generate the second biological sound information in which the first noise information is enhanced.

<3>

In an aspect in which the component that is less than or equal to the predetermined degree of the cepstrum information is removed, as described above, the processing device may be configured to perform a second process of reducing a component that corresponds to a characteristic obtained by averaging a plurality of cepstrum informations in a predetermined period, from each of the plurality of cepstrum informations, before performing the first process.

In this case, the second process is performed before the first process (or the liftering process). The second process is a so-called CMN process, and a regularly incorporated characteristic or a property influenced by a sensor and an environment or the like can be removed from the cepstrum information. The characteristic may be obtained by averaging the plurality of cepstrum informations in the predetermined period (e.g. one breathing cycle).

If the second process is performed before the first process, a sound other than the noise information, i.e., an unnecessary component, can be reduced. It is thus possible to output the more accurate second noise information.

<4>

In an aspect in which the component that corresponds to the characteristic obtained by averaging the ceptstrum informations, as described above, the processing device may be configured to calculate an information amount, which is determined in accordance with a deviation amount of the second biological sound information from a predetermined reference value, for each predetermined section after performing the first process, and said processing device may be configured to generate the second biological sound information by performing a third process of reducing a component in which the information amount is less than or equal to a first threshold value.

In this case, the third process is performed after the first process, by which the second biological sound information is generated. In the third process, the information amount, which is determined in accordance with the deviation amount of the second biological sound information from the predetermined reference value, is calculated for each predetermined section. The "information amount" herein is obtained by numerically expressing or digitizing a characteristic part of the second biological sound information, and an example is a Kullback-Leibler (KL) information amount. If the information amount is calculated, the component in which the information amount is less than or equal to the first threshold value is reduced. The "first threshold value" may be a threshold value for determining that the information amount is small enough to distinguish a part that is not the characteristic part.

According to the third process described above, the component in which the information amount is small (or it is not characteristic) is reduced. Thus, the first noise information, which indicates the noise, is further enhanced.

<5>

In another aspect of the biological sound analyzing apparatus according to the embodiment, the outputting device is configured to calculate a ratio of a period in which the correlation information continuously exceeds a second threshold value for a time that is greater than or equal to a predetermined duration, with respect to a predetermined cycle, and said outputting device is configured to output the second noise information if the ratio of the period is greater than or equal to a predetermined ratio.

According to this aspect, the outputting device is configured to firstly calculate the ratio of the period in which the correlation information continuously exceeds the second threshold value for the time that is greater than or equal to the predetermined duration, with respect to the predetermined cycle (e.g., one breathing cycle). In other words, the ratio of the period in which the correlation information remains relatively high may be calculated. The "second threshold value" may be a threshold value for determining that the correlation information is high enough to distinguish the noise. Moreover, the "predetermine duration" may be a time set for excluding a momentary variation in the correlation information.

The outputting device is further configured to determine whether or not the calculated ratio of the period is greater than or equal to the predetermined ratio. If the calculated ratio of the period is greater than or equal to the predetermined ratio, the second noise information is outputted (i.e., it is determined that the biological sounds include the continuous noise). In other words, if the ratio of the period is less than the predetermined ratio, the second noise information is not outputted (i.e., it is determined that the biological sounds do not include the continuous noise). The "predetermined ratio" may be a value set as a threshold value for determining that the ratio of the period is high enough to detect the noise.

As described above, by using the ratio of the period in which the correlation information is kept high, it is possible to remove a case in which the correlation information is temporarily high. It is thus possible to output the more accurate second noise information.

<6>

In another aspect of the biological sound analyzing apparatus according to the embodiment, the outputting device is configured to output information in which a ratio of a component whose frequency is less than or equal to a predetermine frequency is greater than or equal to a third threshold value, out of the second noise information, as third noise information which indicates rhonchi.

According to this aspect, the outputting device is configured to determine whether or not there is any information in which the ratio of the component whose frequency is less than or equal to the predetermined frequency is greater than or equal to the third threshold value, out of the second noise information. The "predetermined frequency" may be a threshold value for distinguishing a frequency component unique to rhonchi, and may be set as e.g., a value of 120 Hz to 130 Hz. Moreover, the "third threshold value" may be a threshold value for determining whether or not the ratio of the component whose frequency is greater than or equal to the predetermined frequency is high enough to distinguish the rhonchi.

The rhonchi is known as sound that include a relatively low frequency band component among the continuous sounds. Thus, according to the aforementioned determination, it is possible to determine whether or not the continuous sounds are the rhonchi. The third noise information indicating the rhonchi may be outputted with the second noise information, or may be outputted instead of the second noise information.

<7>

A biological sound analyzing method according to an embodiment is provided with: a first obtaining process of obtaining biological sound information, which indicates a change in biological sounds with time; a second obtaining process of obtaining characteristic information, which indicates a characteristic of external noise, which can be included in the biological sound information; and an outputting process of outputting noise information, which indicates noise included in the biological sounds, on the basis of the biological sound information and the characteristic information.

According to the biological sound analyzing method in the embodiment, as in the biological sound analyzing apparatus in the embodiment described above, it is possible to output the accurate noise information.

Even the biological sound analyzing method in the embodiment can also adopt the same various aspects as those of the biological sound analyzing apparatus in the embodiment described above.

<8>

A computer program product according to an embodiment makes a computer perform: a first obtaining process of obtaining biological sound information, which indicates a change in biological sounds with time; a second obtaining process of obtaining characteristic information, which indicates a characteristic of external noise, which can be included in the biological sound information; and an outputting process of outputting noise information, which indicates noise included in the biological sounds, on the basis of the biological sound information and the characteristic information.

According to the computer program in the embodiment, it can make a computer to perform the same processes as those in the biological sound analyzing method in the embodiment described above. It is therefore possible to output the accurate noise information.

Even the computer program in the embodiment can also adopt the same various aspects as those of the biological sound analyzing apparatus in the embodiment described above.

<9>

On a recording medium according to an embodiment, the computer program product described above is recorded.

According to the recording medium in the embodiment, it is possible to output the accurate noise information by making a computer perform the computer program described above.

The operation and other advantages of the biological sound analyzing apparatus, the biological sound analyzing method, the computer program, and the recording medium according to the embodiments will be explained in more detail in the following examples.

EXAMPLES

Hereinafter, a biological sound analyzing apparatus, a biological sound analyzing method, a computer program, and a recording medium according to examples will be explained in detail with reference to the drawings. In the following examples, a biological sound analyzing apparatus configured to analyze breath sounds will be explained.

First Example

Firstly, a biological sound analyzing apparatus according to a first example will be explained with reference to FIG. 1 to FIG. 14.

<Configuration of Apparatus>

Firstly, a configuration of the biological sound analyzing apparatus according to the first example will be explained with reference to FIG. 1. FIG. 1 is a block diagram illustrating the configuration of the biological sound analyzing apparatus according to the first example.

In FIG. 1, the biological sound analyzing apparatus according to the first example is provided with a breath sound acquirer 100, a processor 200, and a result display 300.

The breath sound acquirer 100 may be a sensor configured to obtain breath sounds of a living body as a breath sound signal. The breath sound acquirer 100 is provided with a microphone using e.g., an electrets condenser microphone (ECM) and a piezo microphone, a vibration sensor, and the like.

The breath sound acquirer 100 may be the sensor configured to obtain the breath sounds of the living body as the breath sound signal, but also may include a unit configured to obtain the breath sound signal from the sensor. The breath sound signal obtained by the breath sound acquirer 100 may be outputted to a time-frequency analyzer 210 of the processor 200. The breath sound acquirer 100 is a specific example of the "obtaining device".

The processor 200 may include a plurality of arithmetic circuits and a memory or the like. The processor 200 is provided with the time-frequency analyzer 210, a cepstrum analyzer 220, a noise enhancement processor 230, a correlation information calculator 240, and a continuous sound determinator 250.

The time-frequency analyzer 210 is configured to perform a time-frequency analysis process on breath sound information obtained by the breath sound acquirer 100. Specifically, the time-frequency analyzer 210 is configured to perform a FFT process on the breath sound information. An analysis result of the time-frequency analyzer 210 may be outputted to the cepstrum analyzer 220.

The cepstrum analyzer 220 is configured to convert the breath sound information (or a power spectrum) that is time-frequency-analyzed, to a cepstrum. Specifically, the cepstrum analyzer 220 is configured to perform an inverse Fourier transform on the breath sound information. An analysis result of the cepstrum analyzer 220 may be outputted to the noise enhancement processor 230.

The noise enhancement processor 230 is configured to perform a noise enhancement process of enhancing included noise, on the breath sound information that is converted to the cepstrum. The noise enhancement process may be, for example, a CMN process, a liftering process, or the like. The noise enhancement process will be detailed in Explanation of Operation later. A process result of the noise enhancement processor 230 may be outputted to the correlation information calculator 240. The noise enhancement processor 230 is a specific example of the "processing device".

The correlation information calculator 240 is configured to calculate correction information from the breath sound information on which the noise enhancement process is performed. The correlation information is information indicating a correlation between adjacent frames of the breath sound information, and may be calculated by comparing the cepstrums between the frames. The correlation information calculated by the correlation information calculator 240 may be outputted to the continuous sound determinator 250. The correlation information calculator 240 is a specific example of the "calculating device".

The continuous sound determinator 250 is configured to determine whether or not the breath sounds include continuous sounds on the basis of the correlation information. Specifically, the continuous sound determinator 250 is configured to calculate a continuous sound tendency, which indicates characteristics of the continuous sounds, by using the correlation information, and is configured to determine whether or not the breath sounds include the continuous sounds. A determination result of the continuous sound determinator 250 may be outputted to the result display 300. The continuous sound determinator 250 is a specific example of the "outputting device".

As described above, the processor 200 can determine whether or not biological sounds include the continuous sounds, on the basis of the breath sound information obtained by the breath sound acquirer 100. The processor 200 may not only be configured to determine whether or not the biological sounds include the continuous sounds, but also be configured to output the intensity of the continuous sounds, or the like.

The result display 300 is configured as a display, such as, for example, a liquid crystal monitor, and is configured to display various information outputted from the processor 200 as image data.

<Explanation of Operation>

Figure 2:
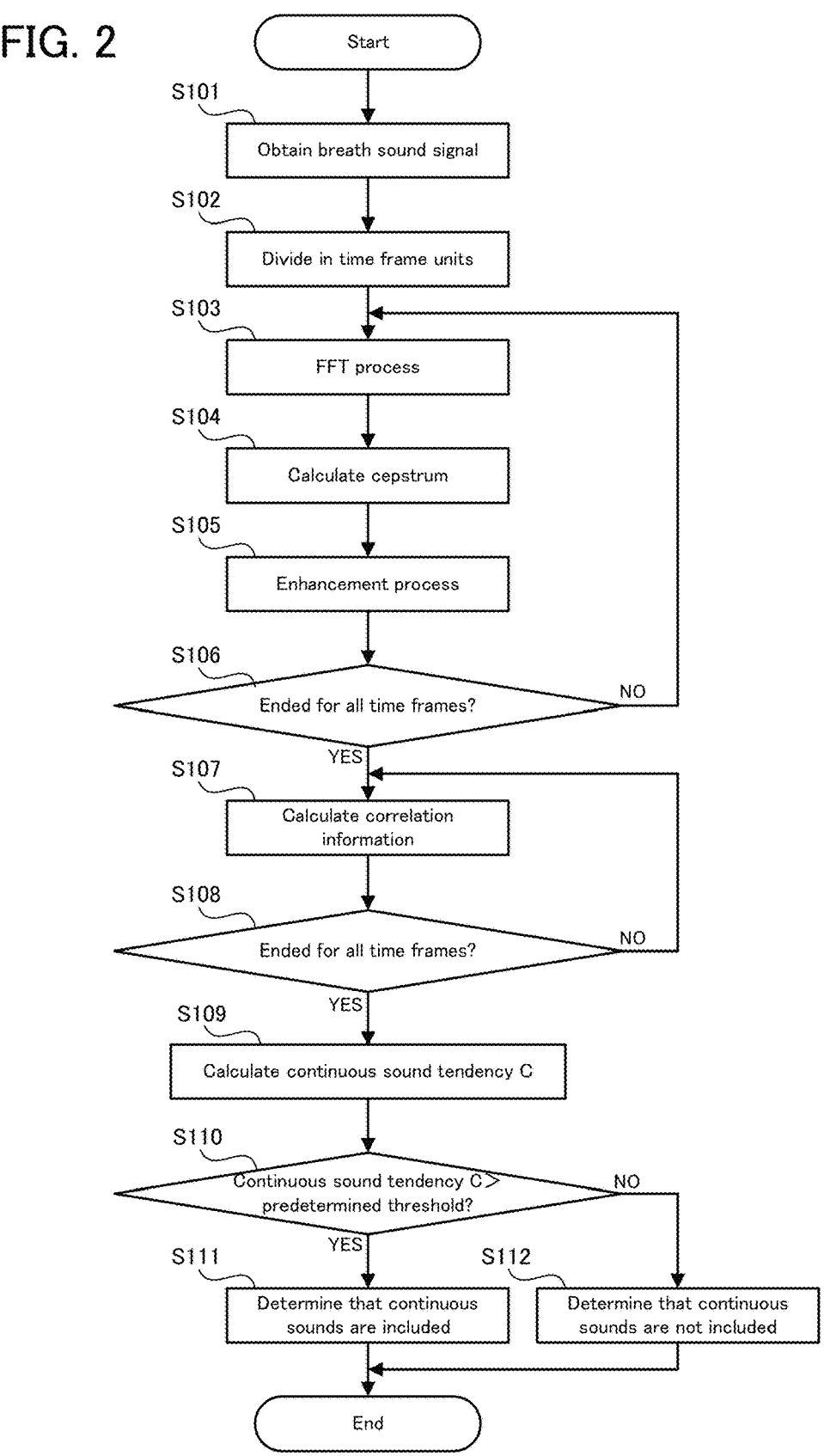
FIG. 2 is a flowchart illustrating a flow of operations of the biological sound analyzing apparatus according to the example.

Next, operations of the biological sound analyzing apparatus according to the example will be explained with reference to FIG. 2. FIG. 2 is a flowchart illustrating a flow of the operations of the biological sound analyzing apparatus according to the first example.

In FIG. 2, in operation of the biological sound analyzing apparatus according to the first example, firstly, the breath sound signal indicating the breath sounds of the living body is obtained on the breath sound acquirer 100 (step S101). If the breath sound signal is obtained, the breath sound signal is divided in predetermined time frame units on the time-frequency analyzer 210 (step S102), and the time-frequency analysis by the FFT process is performed (step S103).

Figure 3:
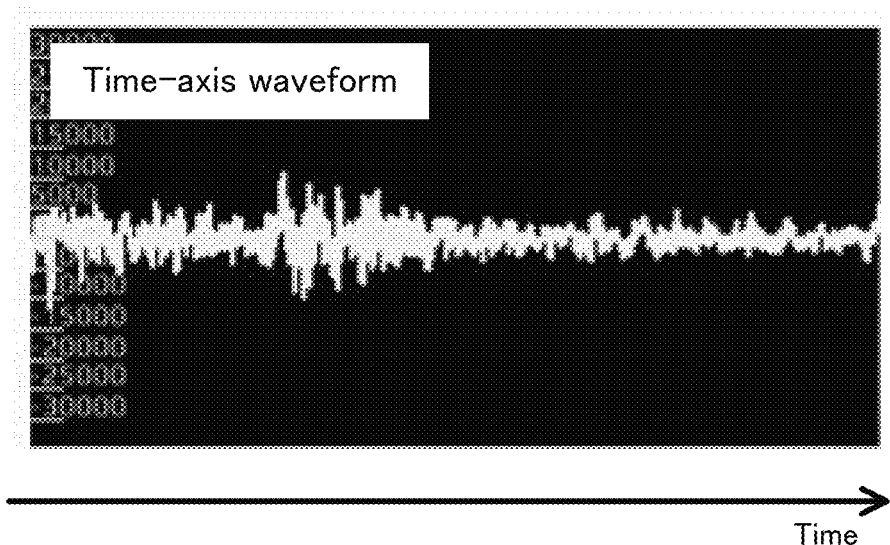
FIG. 3 is a waveform diagram illustrating an example of a time-axis waveform of breath sounds.
Figure 4:
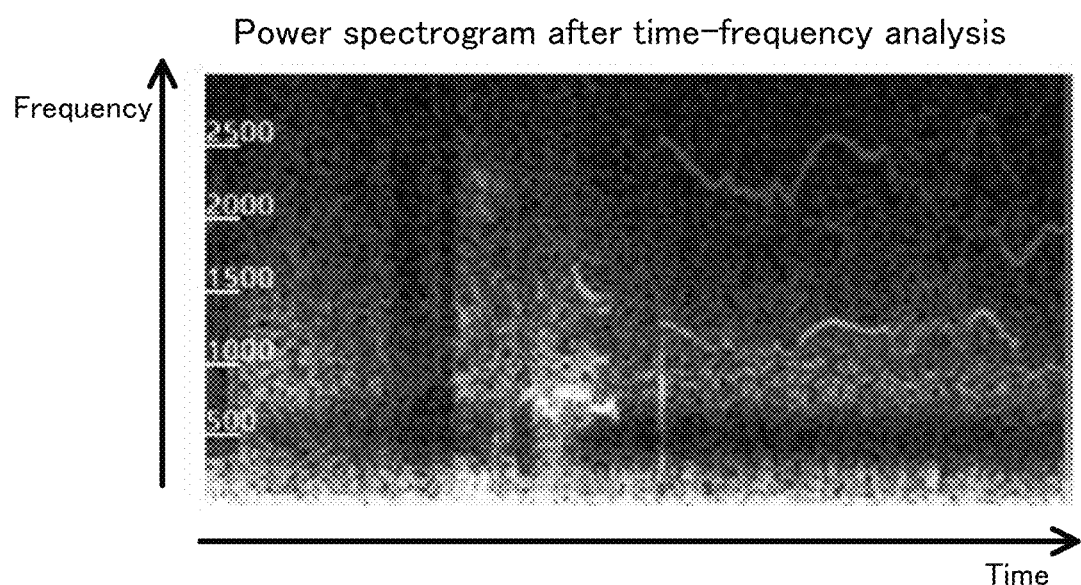
FIG. 4 is a power spectrogram illustrating an example of a power spectrum of the breath sounds.

Hereinafter, the time-frequency analysis of the breath sound signal will be explained in detail with reference to FIG. 3 and FIG. 4. FIG. 3 is a waveform diagram illustrating an example of a time-axis waveform of the breath sounds. FIG. 4 is a power spectrogram illustrating an example of a power spectrum of the breath sounds.

As illustrated in FIG. 3, the breath sound information may be obtained as a time-axis waveform. The time-axis waveform is a specific example of the "first biological sound information". When the time-axis waveform is time-frequency-analyzed to obtain the power spectrum, an N-point short-time Fourier transform and a logarithmic transformation may be firstly performed on a value x(n) at a time point n of the time-axis waveform in units of frames, each of which has a length N. By this, a time-frequency-analyzed waveform P Log [n,ω] is calculated. When the frame is cut out, a window function w(m) with a length N may be used.

More specifically, the N-point short-time Fourier transform may be performed by using the following equation (1).

[Equation 1]

$$STFT[n,\omega]=\Sigma_{m=0}^{N-1}x(n+m)w(m)e^{-j\omega m} \quad (1)$$

Moreover, the logarithmic transformation may be performed by using the following equation (2).

[Equation 2]

$$P\,Log\,[n,\omega]=20\,\log_{10}|STFT[n,\omega]| \quad (2)$$

As illustrated in FIG. 4, the time-frequency-analyzed waveform P Log [n,ω] may be obtained as a spectrogram with time on a horizontal axis and with frequency on a vertical axis. Shade of the spectrogram indicates power, and a brighter part has a higher power.

Back in FIG. 2, the time-frequency-analyzed waveform P Log [n,ω] obtained by the time-frequency analysis of the breath sound information, i.e., the power spectrum, is converted to the cepstrum on the cepstrum analyzer 220 (step S104).

Figure 5:
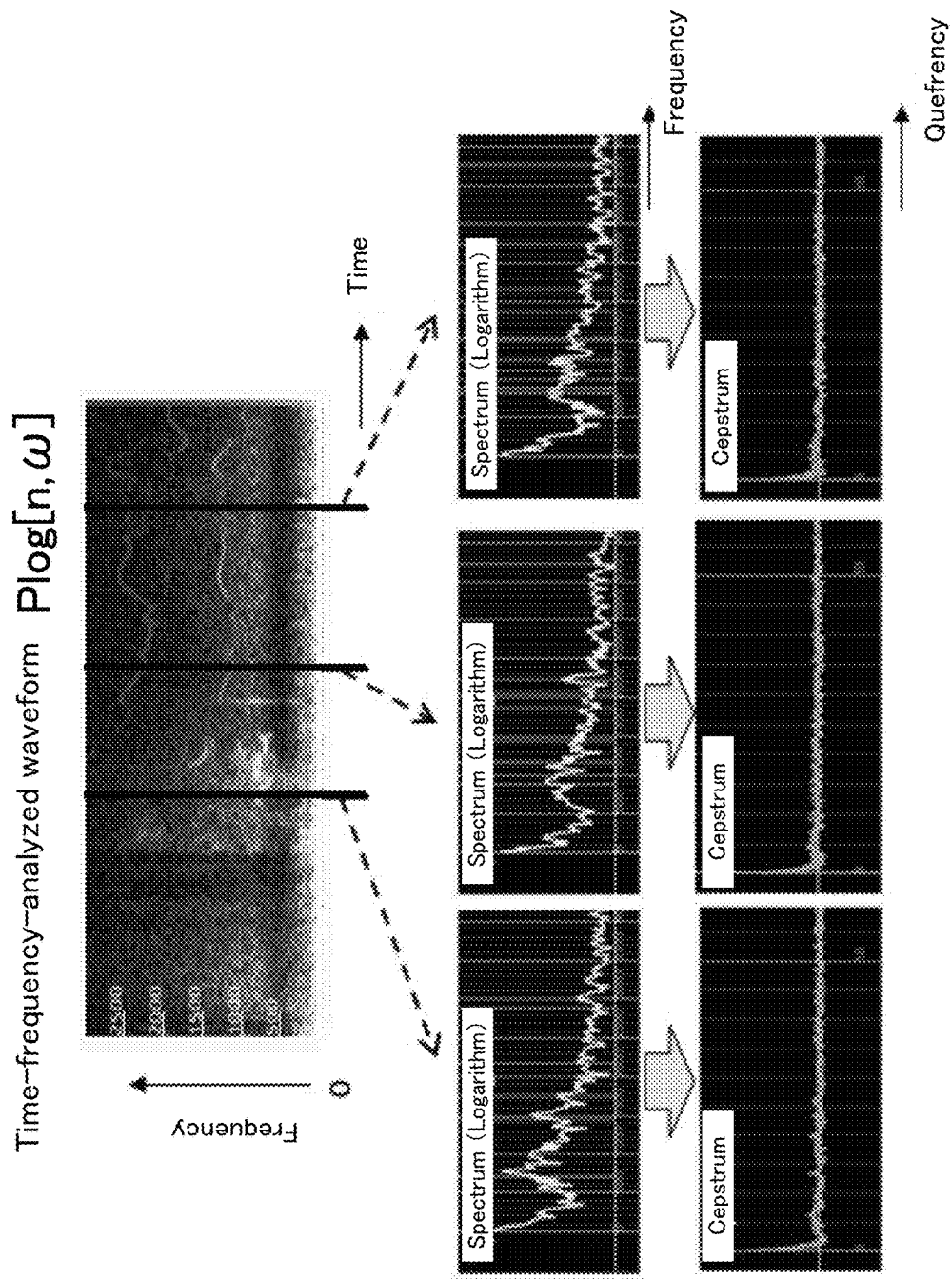
FIG. 5 is a process diagram illustrating a method of converting the power spectrum to a cepstrum.

Hereinafter, a method of converting the power spectrum to the cepstrum will be explained in detail with reference to FIG. 5. FIG. 5 is a process diagram illustrating the method of converting the power spectrum to the cepstrum.

As illustrated in FIG. 5, when the power spectrum is converted to the cepstrum, the inverse Fourier transform may be performed on the power spectrum (log scale) at each time point n to calculate a cepstrum C[n,l]. Specifically, the following equation (3) may be calculated.

[Equation 3]

$$C[n,l]=\frac{1}{N}\sum_{\omega=0}^{N-1}P\text{Log}[n,\omega]e^{j\omega l} \quad (3)$$

Wherein l is a degree on a discretized quefrency, and l=0, . . . , N.

By using the cepstrum obtained in this manner, the noise enhancement process and the calculation of a correlation coefficient, which will be described later, can be preferably performed.

If the cepstrum is inversely transformed to the power spectrum, the following equation (4) may be calculated.

[Equation 4]

$$P\,Log\,[n,\omega]=\Sigma_{l=0}^{N-1}C[n,l]e^{-j\omega l} \quad (4)$$

Back in FIG. 2, if the cepstrum is obtained, the noise enhancement process for enhancing the noise included in the breath sounds is performed on the noise enhancement processor 230 (step S105). In the first example, a CMN process and a liftering process are performed as the noise enhancement process.

Figure 6:
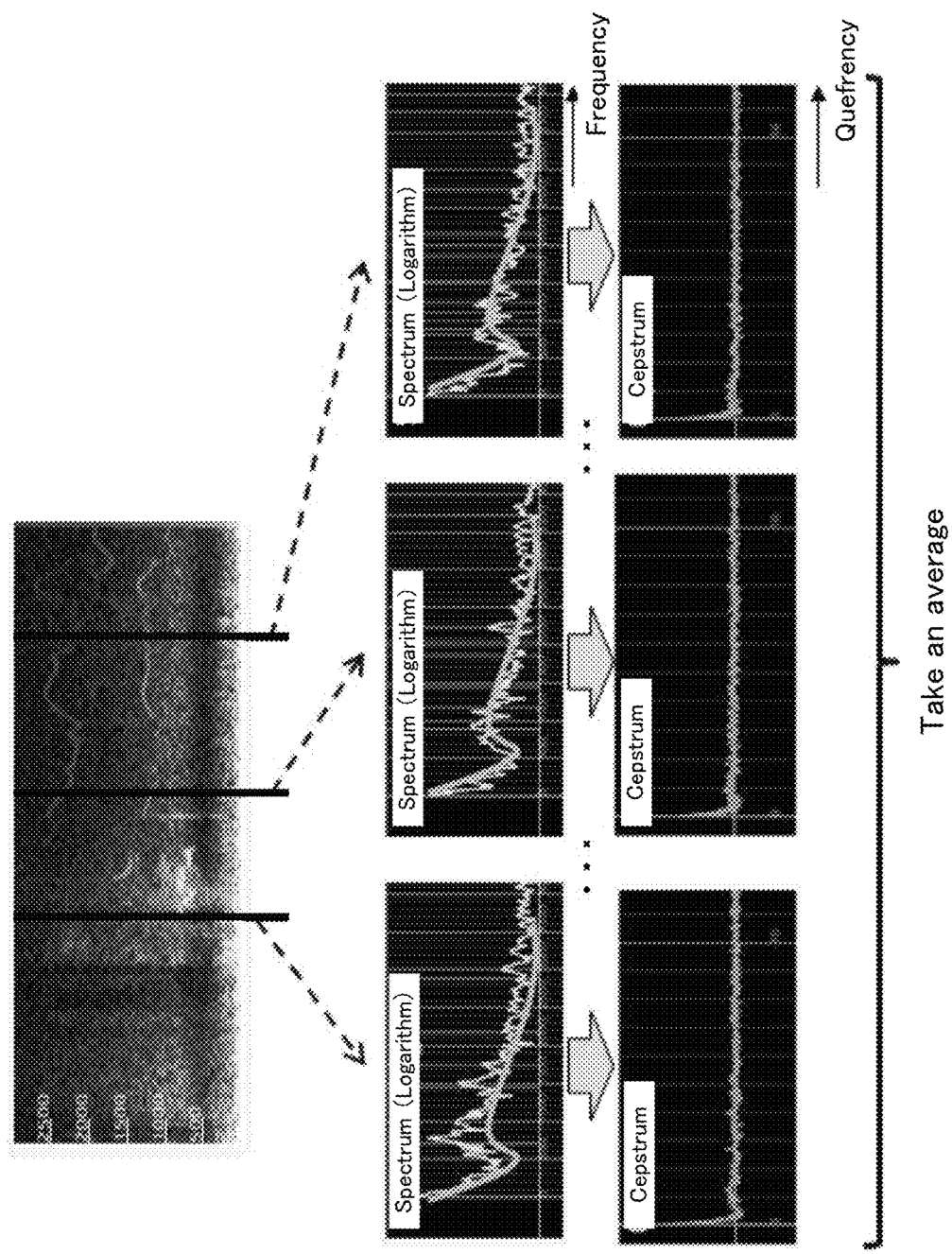
FIG. 6 is a process diagram illustrating a CMN process.
Figure 7:
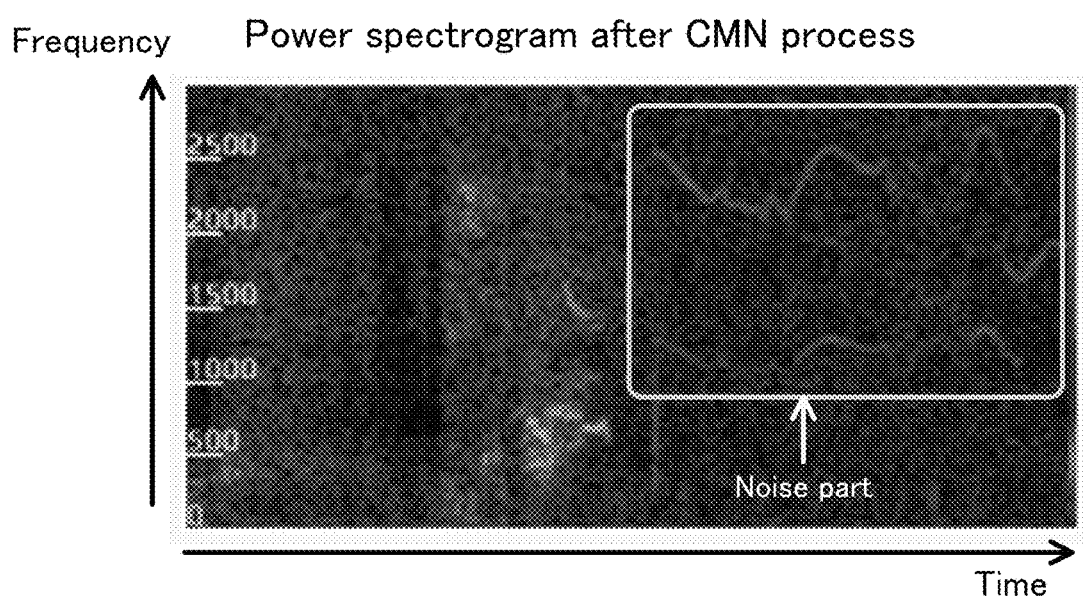
FIG. 7 is a power spectrogram illustrating an example of a power spectrum after the CMN process.
Figure 8:
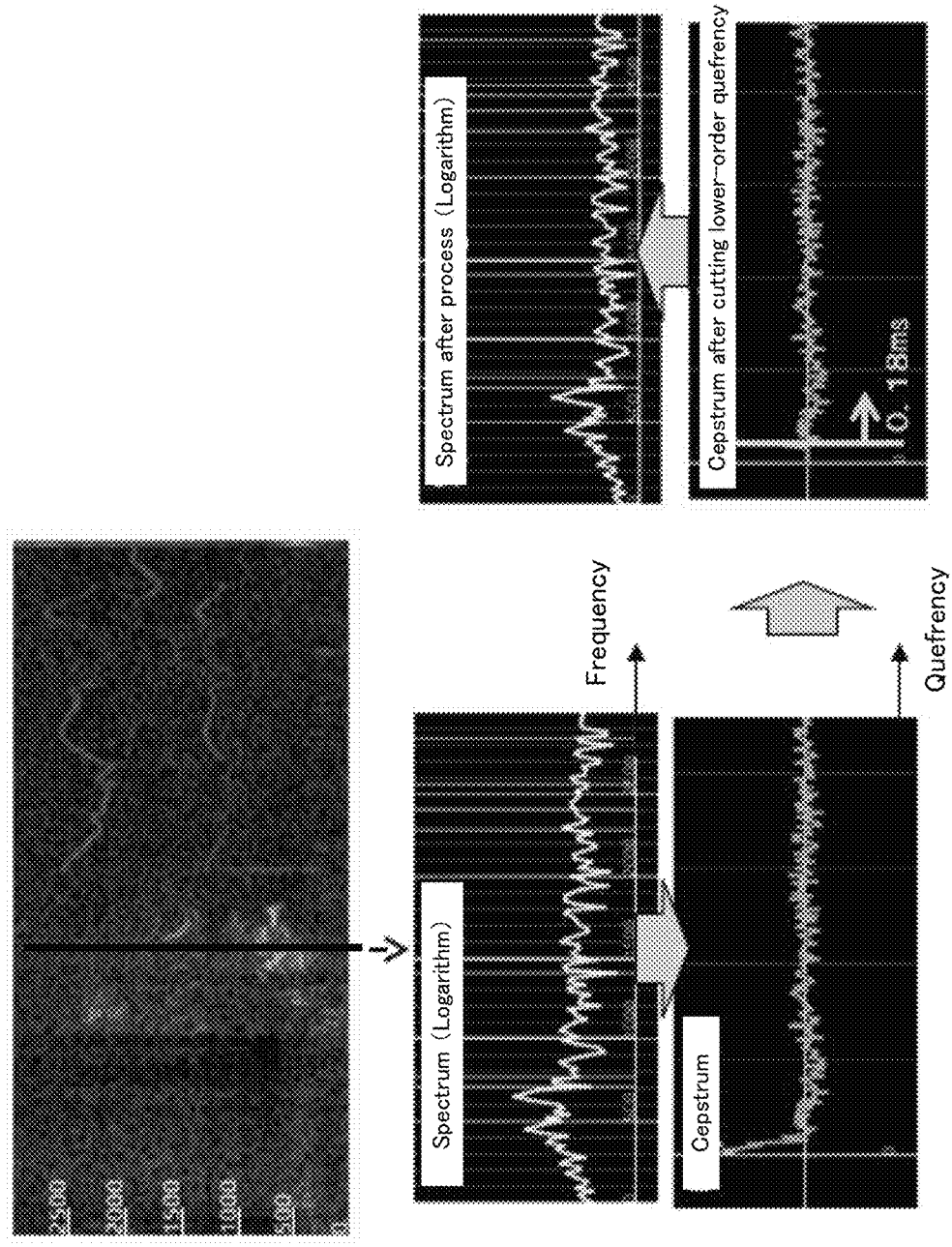
FIG. 8 is a process diagram illustrating a liftering process.
Figure 9:
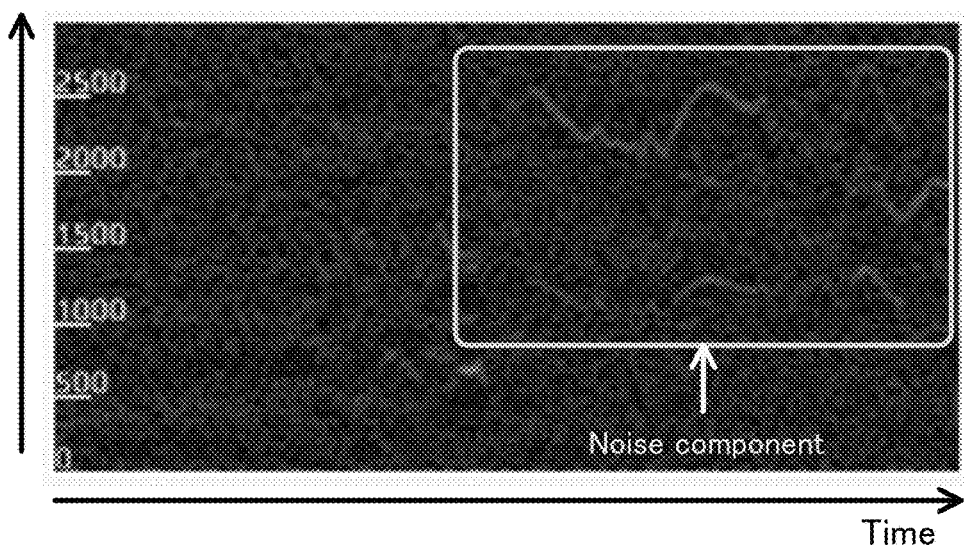
FIG. 9 is a power spectrogram illustrating an example of a power spectrum after the liftering process.

Hereinafter, the CMN process and the liftering process will be explained in detail with reference to FIG. 6 to FIG. 9. FIG. 6 is a process diagram illustrating the CMN process. FIG. 7 is a power spectrogram illustrating an example of a power spectrum after the CMN process. FIG. 8 is a process diagram illustrating the liftering process. FIG. 9 is a power spectrogram illustrating an example of a power spectrum after the liftering process.

As illustrated in FIG. 6, the CMN process may be firstly performed on the cepstrum on the noise enhancement processor 230. The CMN process is a specific example of the "second process".

In the CMN process, a regularly incorporated characteristic or a property of a sensor and an environment or the like may be canceled, i.e., removed, from the cepstrum. The characteristic $C_{mean}[l]$ may be calculated by using the following equation (5).

[Equation 5]

$$C_{mean}[l] = \frac{1}{n_{end}} \sum_{n=0}^{n_{end}} C[n, l] \quad (5)$$

The calculated characteristic $C_{mean}[l]$ may be subtracted from the cepstrum $C[n,l]$ as in the following equation (6).

[Equation 6]

$$C'[n,l] = C[n,l] - C_{mean}[l] \quad (6)$$

$C'[n,l]$ obtained in this manner has the noise that is enhanced by removing the regularly incorporated characteristic.

As illustrated in FIG. 7, if the cepstrum $C'[n,l]$ after the CMN process is inversely transformed to the power spectrum, it is clear that a noise part is enhanced in comparison with the power spectrum before the CMN process, which is illustrated in FIG. 4.

As illustrated in FIG. 8, the liftering process may be performed after the CMN process. The liftering process is a specific example of the "first process".

In the liftering process, a quefrency component whose degree is less than or equal to a predetermined degree may be cut from the cepstrum. The predetermined degree may be adjusted to a value that allows the continuous sounds to be enhanced. In the example illustrated in FIG. 8, a component whose quefrency is less than or equal to 0.18 ms is cut.

In order to realize the aforementioned liftering process, the following equation (7) may be calculated after an appropriate cut degree lift is determined.

[Equation 7]

$$C''[n,l] = C'[n,l] \quad l = \text{lift}, \ldots, N-\text{lift}$$

$$C''[n,l] = 0 \quad l = 0, \ldots, \text{lift}-1, N-\text{lift}+1, \ldots, N-1 \quad (7)$$

According to the liftering process, a flat component of a frequency characteristic is cut, so that a relatively sharp component is enhanced.

As illustrated in FIG. 9, if the cepstrum $C''[n,l]$ after the liftering process is inversely transformed to the power spectrum, it is clear that a noise part is further enhanced in comparison with the power spectrum before the liftering process, which is illustrated in FIG. 7.

As described above, by performing the CMN process and the liftering process, it is possible to enhance the noise included in the breath sound information. Noise information enhanced by the CMN process and the liftering process is a specific example of the "first noise information", and the breath sound information after the CMN process and the liftering process is a specific example of the "second biological sound information".

Back in FIG. 2, if the enhancement process is ended, it is determined whether or not the enhancement process is ended for all the time frames (step S106). If the enhancement process is not ended for all the time frames (the step S106: NO), the process after the step S103 is repeated for the other time frames. On the other hand, if the enhancement process is ended for all the time frames (the step S106: YES), the correlation information is calculated on the correlation information calculator 240 (step S107).

Figure 10:
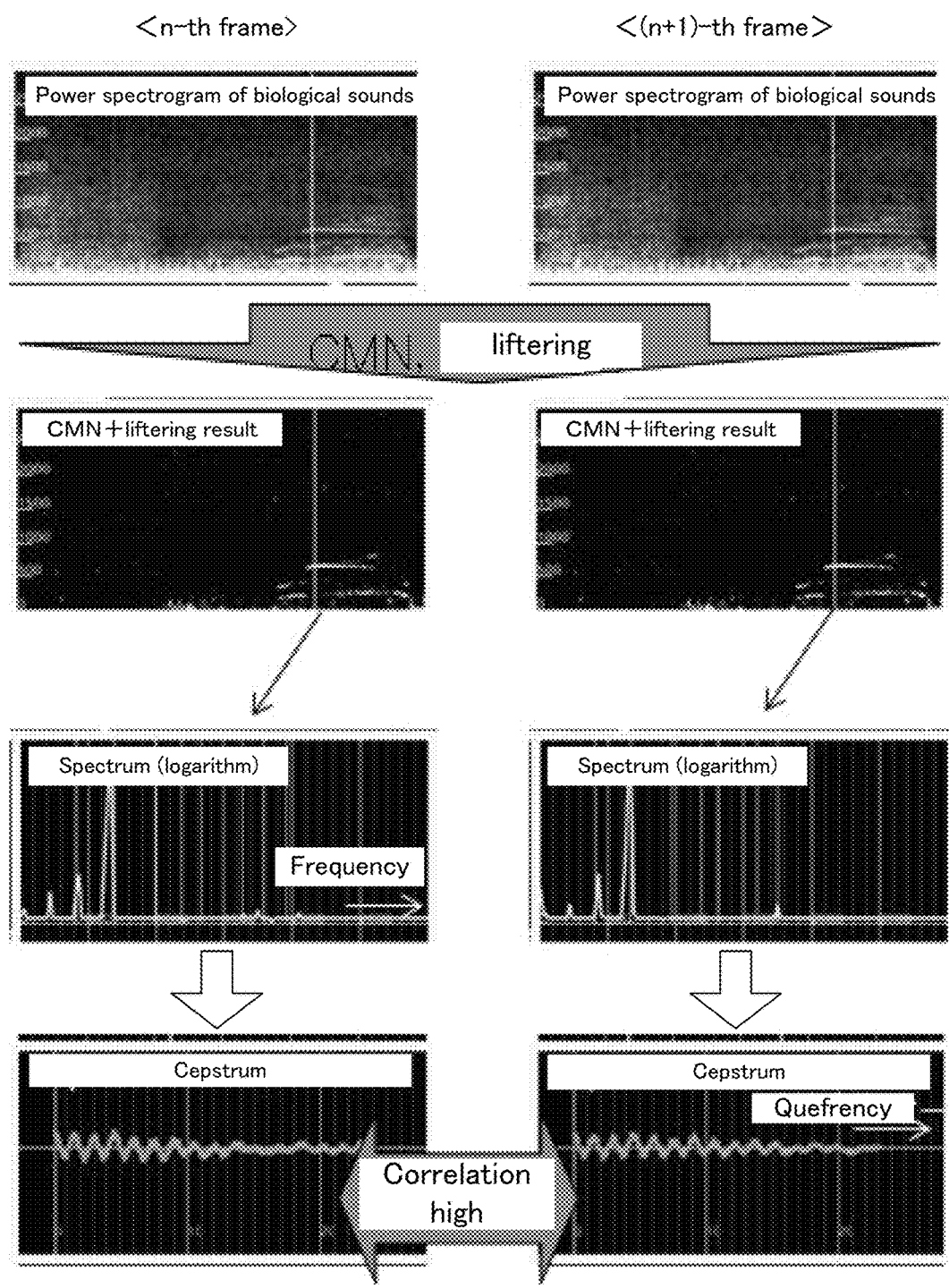
FIG. 10 is a process diagram illustrating a method of calculating a correlation coefficient between adjacent frames in a section in which continuous sounds are generated.
Figure 11:
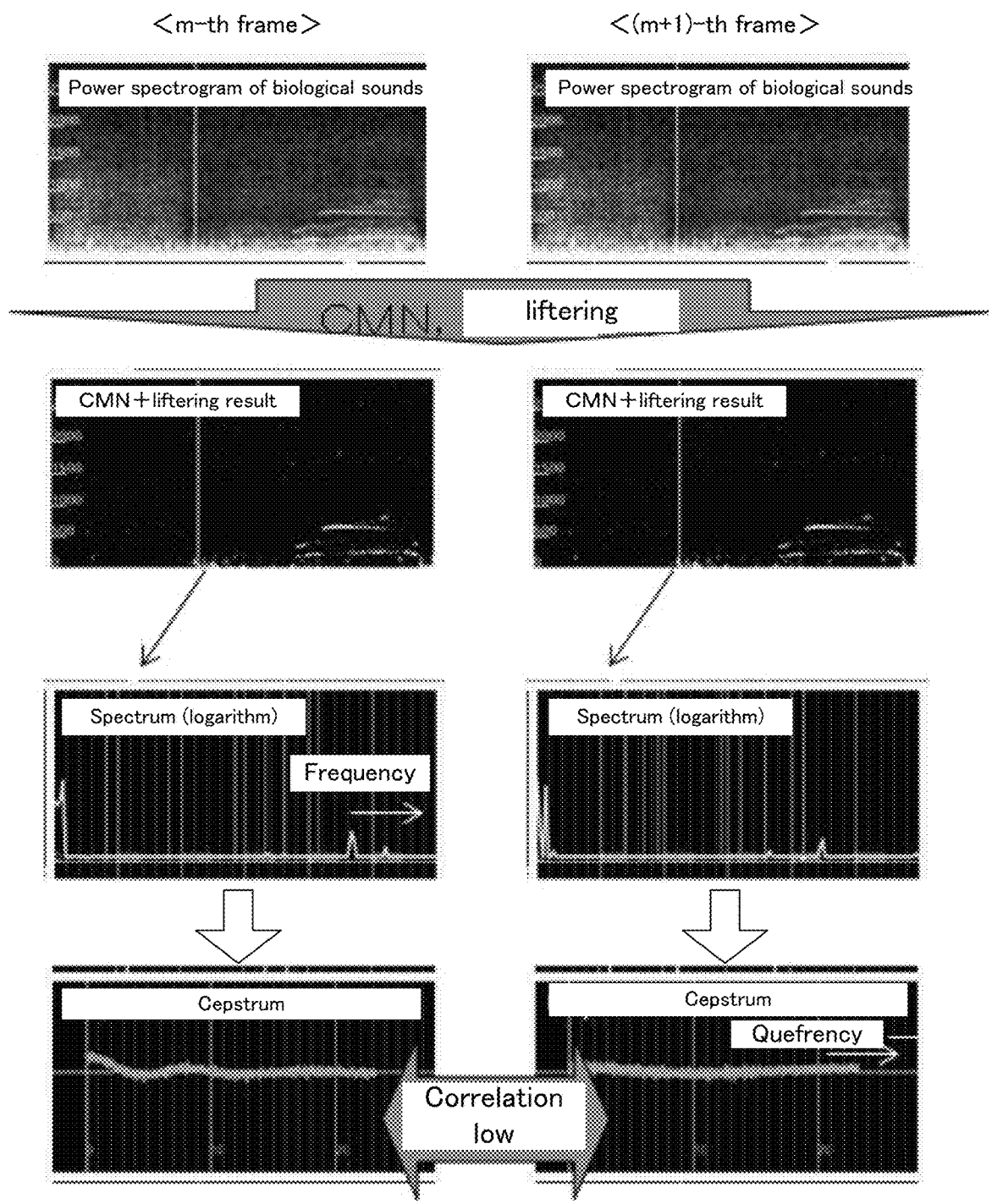
FIG. 11 is a process diagram illustrating a method of calculating a correlation coefficient between adjacent frames in a section in which continuous sounds are not generated.
Figure 12:
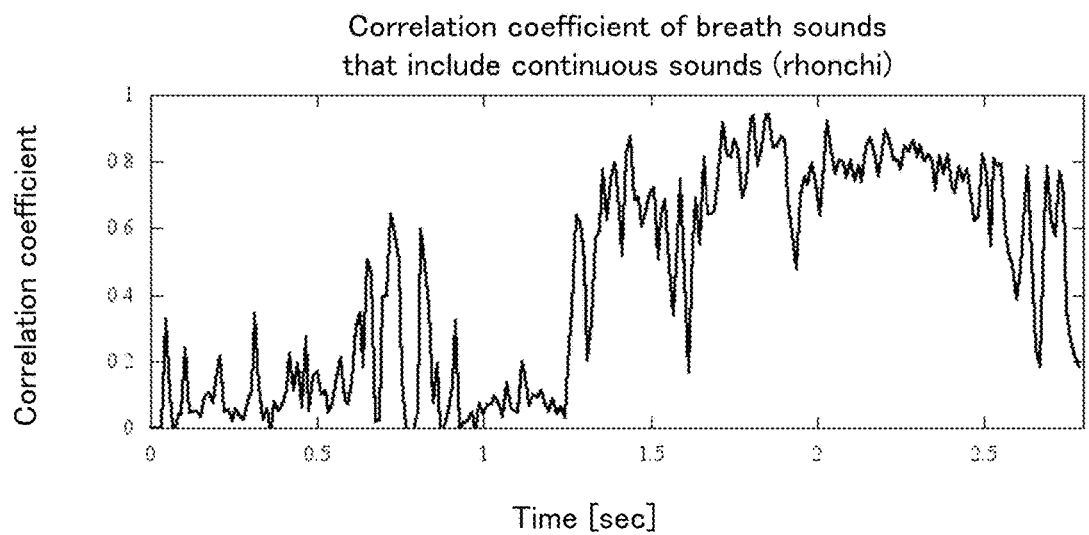
FIG. 12 is a graph illustrating an example of a correlation coefficient of the breath sounds that include the continuous sounds.
Figure 13:
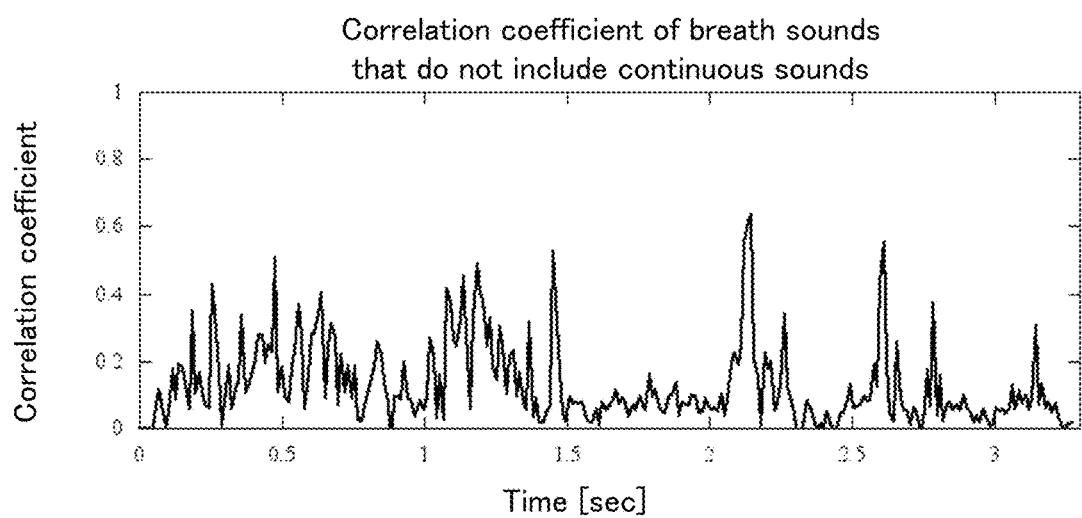
FIG. 13 is a graph illustrating an example of a correlation coefficient of the breath sounds that do not include the continuous sounds.

Hereinafter, a method of calculating the correlation information will be explained in detail with reference to FIG. 10 to FIG. 13. FIG. 10 is a process diagram illustrating a method of calculating a correlation coefficient between adjacent frames in a section in which the continuous sounds are generated. FIG. 11 is a process diagram illustrating a method of calculating a correlation coefficient between adjacent frames in a section in which the continuous sounds are not generated. FIG. 12 is a graph illustrating an example of a correlation coefficient of the breath sounds that include the continuous sounds. FIG. 13 is a graph illustrating an example of a correlation coefficient of the breath sounds that do not include the continuous sounds.

As illustrated in FIG. 10 and FIG. 11, the correlation information may be calculated as a correlation coefficient indicating a correlation between frames adjacent to each other on a time axis, e.g., between an n-th frame and an (n+1)-th frame.

Here, in particular, the number of peaks is extremely small on a spectrum frequency axis; for example, the number of peaks is 3 with respect to the number of frequency divisions of 1024. Moreover, the continuous sounds have a characteristic frequency that can change with time. When correlation is obtained for spectra between the adjacent frames, even a small number of different peak frequency positions cause the correlation coefficient to have a low value despite a continuous change. In contrast, the conversion to the cepstrum causes information about a harmonic structure to appear on an entire quefrency axis. Thus, an influence of a change in the peak frequency may be reduced, and the level of the correlation between the adjacent frames can be accurately numerically expressed or digitized.

Specifically, the continuous sounds are included at a time point corresponding to the n-th frame of the breath sounds illustrated in FIG. 10. In this case, the correlation coefficient is calculated as a high value. On the other hand, the continuous sounds are not included at a time point corresponding to an m-th frame of the breath sounds illustrated in FIG. 11. Thus, the correlation coefficient is calculated as a low value.

As illustrated in FIG. 12, the correlation coefficient of the breath sounds that include rhonchi, which are the continuous sounds, has a part in which the value is continuously high. On the other hand, the correlation coefficient of the breath sounds that do not include the continuous sounds does not have a part in which the value is continuously high, unlike FIG. 12. Even from the above result, it is clear that the correlation efficient is valid as a parameter for determining the continuous sounds.

Back in FIG. 2, if the correlation information is calculated, it is determined whether or not the correlation information is calculated for all the time frames (step S108). If the correlation information is not calculated for all the time frames (the step S108: NO), the step S107 is performed for the other time frames. On the other hand, if the correlation information is calculated for all the time frames (the step S108: YES), a continuous sound tendency $C_1$ is calculated on the continuous sound determinator 250 (step S109).

Figure 14:
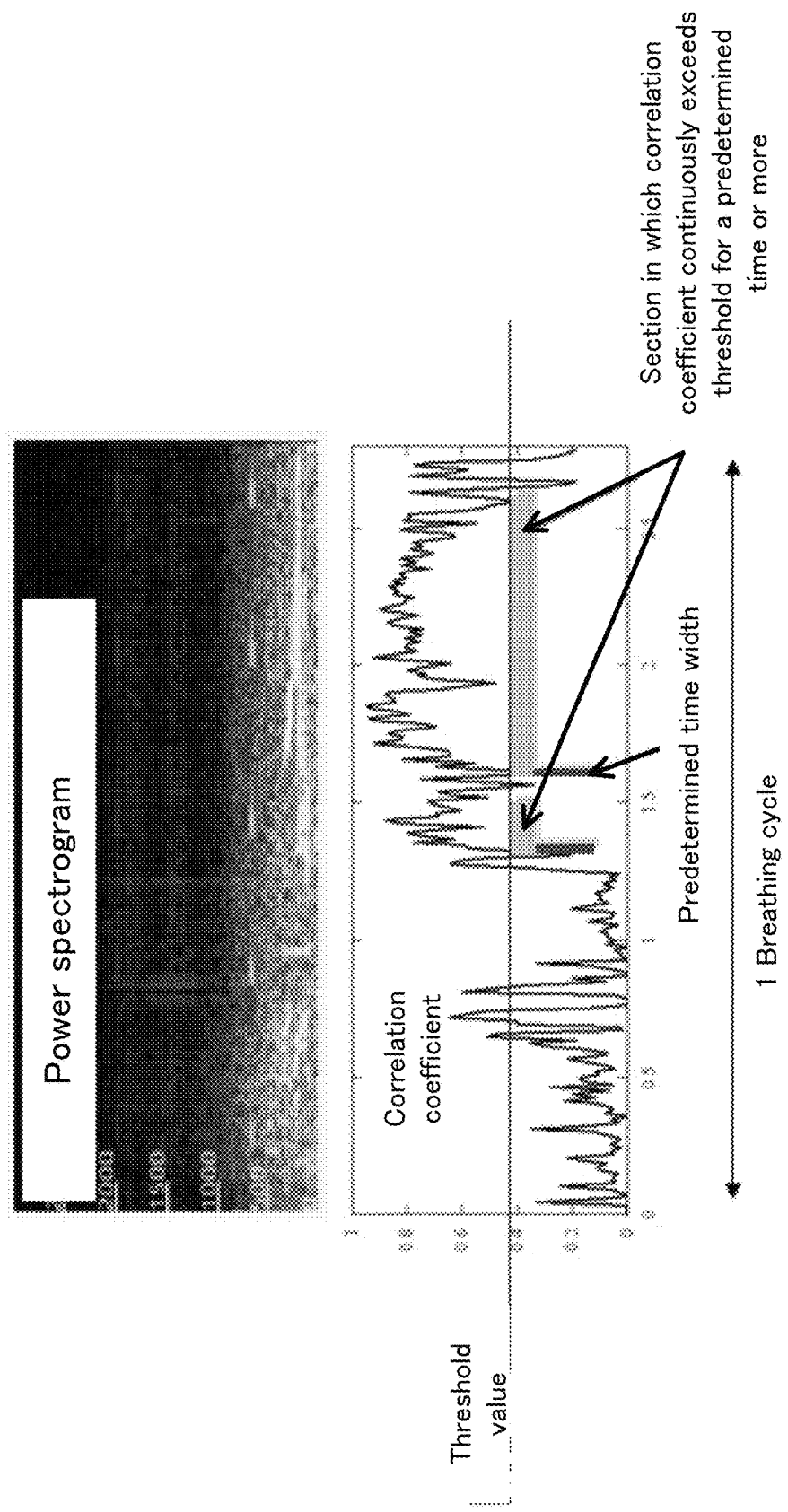
FIG. 14 is a conceptual diagram illustrating a method of calculating a continuous sound tendency.

Hereinafter, a method of calculating the continuous sound tendency $C_1$ will be explained in detail with reference to FIG. 14. FIG. 14 is a conceptual diagram illustrating the method of calculating the continuous sound tendency.

As illustrated in FIG. 0.14, the continuous sound tendency $C_1$ may be calculated as a ratio of a period in which a correlation coefficient $P(t)$ continuously exceeds a predetermined threshold value $P_{thre}$ for a time that is greater than or equal to a predetermined duration, with respect to one breathing cycle. The threshold value $P_{thre}$ is a specific example of the "second threshold value", and the predetermined duration is a specific example of the "predetermined time".

More specifically, when the continuous sound tendency $C_1$ is calculated, a function g(t) may be used, wherein the function g(t) is "1" when the correlation coefficient P(t) exceeds the predetermined threshold value $P_{thre}$, and the function g(t) is "0" when the correlation coefficient P(t) is less than or equal to the predetermined threshold value $P_{thre}$. The continuous sound tendency $C_1$ may be calculated by using the function g(t) and the following equation (8).

[Equation 8]

$$C_1 = \frac{1}{T}\int_0^T g(t)dt \quad (8)$$

It is determined whether or not the calculated continuous sound tendency $C_1$ is greater than a predetermined threshold value $C_{thre}$ (step S110). The threshold value $C_{thre}$ may be a threshold value for determining whether or not the continuous sound tendency $C_1$ is sufficiently high, and may be set in advance on the basis of actual data of the continuous sounds, or the like.

If it is determined that the calculated continuous sound tendency $C_1$ is greater than the predetermined threshold value $C_{thre}$ (the step S110: YES), it is determined that the breath sounds include the continuous sounds (step S111).

On the other hand, if it is determined that the calculated continuous sound tendency $C_1$ is not greater than the predetermined threshold value $C_{thre}$ (the step S110: NO), it is determined that the breath sounds do not include the continuous sounds (step S112).

A determination result by a series of process operations explained above may be outputted to the result display 300. By this, information indicating whether or not the biological sounds include the continuous sounds may be displayed on the result display 300. The information indicating whether or not the biological sounds include the continuous sounds is a specific example of the "second noise information".

Effect of First Example

Next, a technical effect obtained by the biological sound analyzing apparatus according to the first example explained above will be explained.

According to the biological sound analyzing apparatus according to the first example, the noise included in the breath sound information is enhanced, and it is then determined whether or not there is the continuous sound tendency by using the correlation coefficient. The correlation coefficient is, as explained above, a parameter that indicates temporal continuity. It is thus possible to detect a peak component hidden in the noise and a peak component in which the frequency continuously changes in an unsteady manner, by using the correlation coefficient. As a result, it is possible to reduce an influence of the noise caused by an environment or the like, and it is possible to accurately determine the continuous sounds.

Second Example

Next, a biological sound analyzing apparatus according to a second example will be explained with reference to FIG. 15 to FIG. 19. The second example is mostly the same as the first example explained above, and is partially different in configuration and operation. Thus, a different part from that of the first example will be explained in detail, and an explanation of the other same part will be omitted, as occasion demands.

Difference from First Example

The biological sound analyzing apparatus according to the second example is different from that in the first example in the noise enhancement process. Specifically, the second example is configured in such a manner that a process using a KL information amount can be performed, in addition to the CMN process and the liftering process, as the noise enhancement process.

<Enhancement Process Using KL Information Amount>

Figure 15:
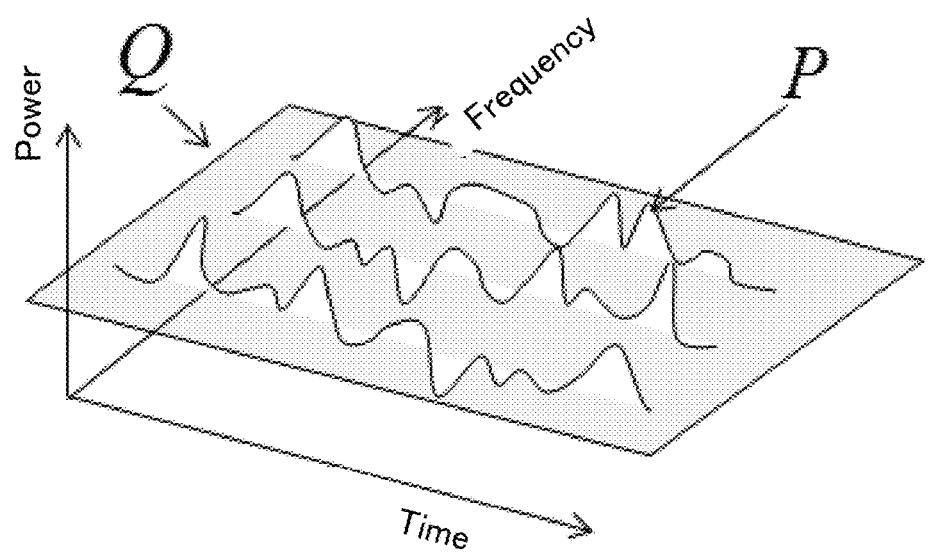
FIG. 15 is version 1 of a three-dimensional graph illustrating a concept of numerically expressing or digitizing a KL information amount.
Figure 16:
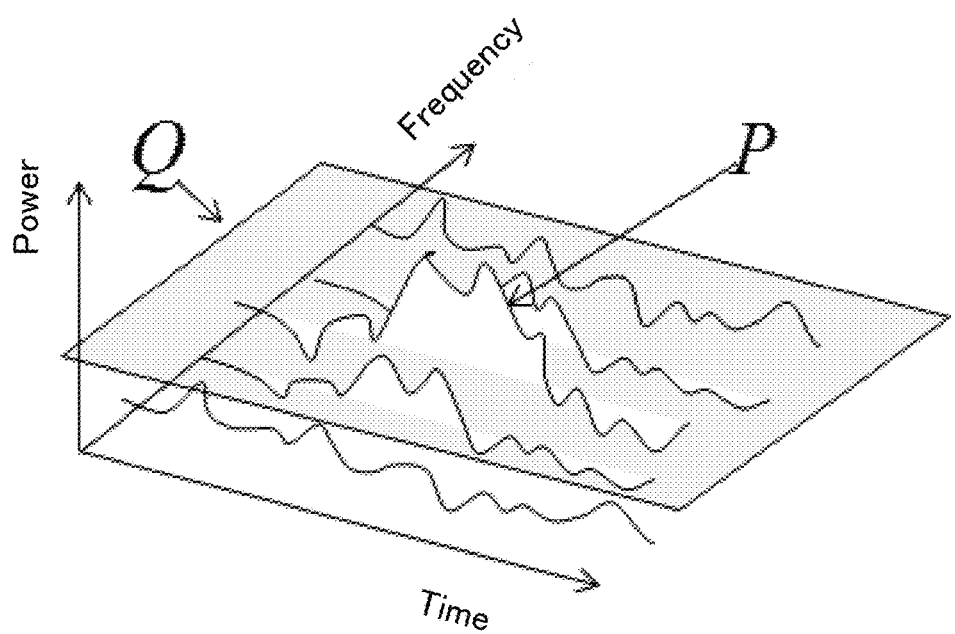
FIG. 16 is version 2 of the three-dimensional graph illustrating the concept of digitizing the KL information amount.
Figure 17:
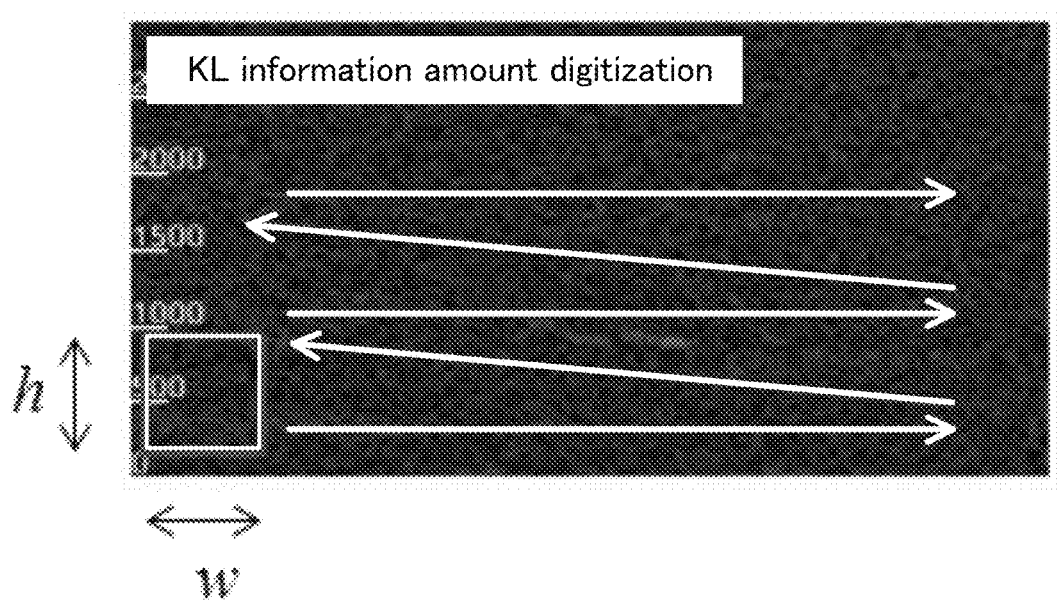
FIG. 17 is a conceptual diagram illustrating a method of calculating the KL information amount.

Hereinafter, the enhancement process using the KL information amount will be specifically explained with reference to FIG. 15 to FIG. 17. Each of FIG. 15 and FIG. 16 is a three-dimensional graph illustrating a concept of numerically expressing or digitizing the KL information amount. FIG. 17 is a conceptual diagram illustrating a method of calculating the KL information amount.

The KL information amount may be a parameter calculated by using an observation value P and a reference value Q (e.g., a theoretical value, a model value, a predictive value, etc.). If the observation value P, which is characteristic to the reference value Q, appears, the KL information amount may be calculated as a large value. A KL information amount $D_{KL}$ can be calculated by using the following equation (9).

[Equation 9]

$$D_{KL}(P\|Q) = \sum_i P(i)\log\frac{P(i)}{Q(i)} \quad (9)$$

In the second example, a power distribution on the spectrogram may be regarded as a probability distribution to calculate the KL information amount $D_{KL}$. For the calculation of the KL information amount $D_{KL}$, a spectrum power Power[n,ω] that is subject to the CMN process and the liftering process may be used, wherein n is a discretized time point index, and ω is a discretized frequency index. Another physical quantity that has information about a time-frequency domain (e.g., an amplitude spectrum) may be used for the calculation.

As illustrated in FIG. 17, in order to calculate a local KL information amount, a predetermined time-direction width w and a predetermined frequency-direction width h are set in advance. Then, the frame is used to sequentially scan a spectrogram along arrows in FIG. 17, by which information about the vicinity of a point [n,ω] on each time-frequency domain is digitized.

First, each of the following equations (10) and (11) is calculated by using a point [i,j] (i=n−w/2, . . . , n+w/2, j=ω−h/2, . . . , ω+h/2) located in the vicinity of [n,ω], and the reference value Q[i,j] and the observation value P[i,j] are obtained.

[Equation 10]

$$Q[i, j] = \frac{1}{w \cdot h} \quad (10)$$

[Equation 11]

$$P[i, j] = \frac{1}{\sum_{k=n-w/2}^{k=n+w/2} \sum_{l=\omega-h/2}^{l=\omega+h/2} \text{Power}[k, l]} \text{Power}[i, j] \quad (11)$$

Then, the calculated Q[i,j] and P[i,j] are used to calculate the following equation (12), thereby to calculate the KL information amount $D_{KL}$. This may be calculated for all n and ω.

[Equation 12]

$$D[n, \omega] = \sum_{i=n-w/2}^{i=n+w/2} \sum_{j=\omega-h/2}^{j=\omega+h/2} P[i, j] \log \frac{P[i, j]}{Q[i, j]} \quad (12)$$

The calculated KL information amount $D_{KL}$ may be compared with a predetermined threshold value $D_{thre}$, and a component in which the KL information amount $D_{KL}$ is less than or equal to the threshold value $D_{thre}$ may be cut. By this, a component in which the KL information amount $D_{KL}$ is greater than the threshold value $D_{thre}$ may be emphasized. The threshold value $D_{thre}$ is a specific example of the "first threshold value", and the enhancement process using the KL information amount $D_{KL}$ is a specific example of the "third process".

Effect of Second Example

Figure 18:
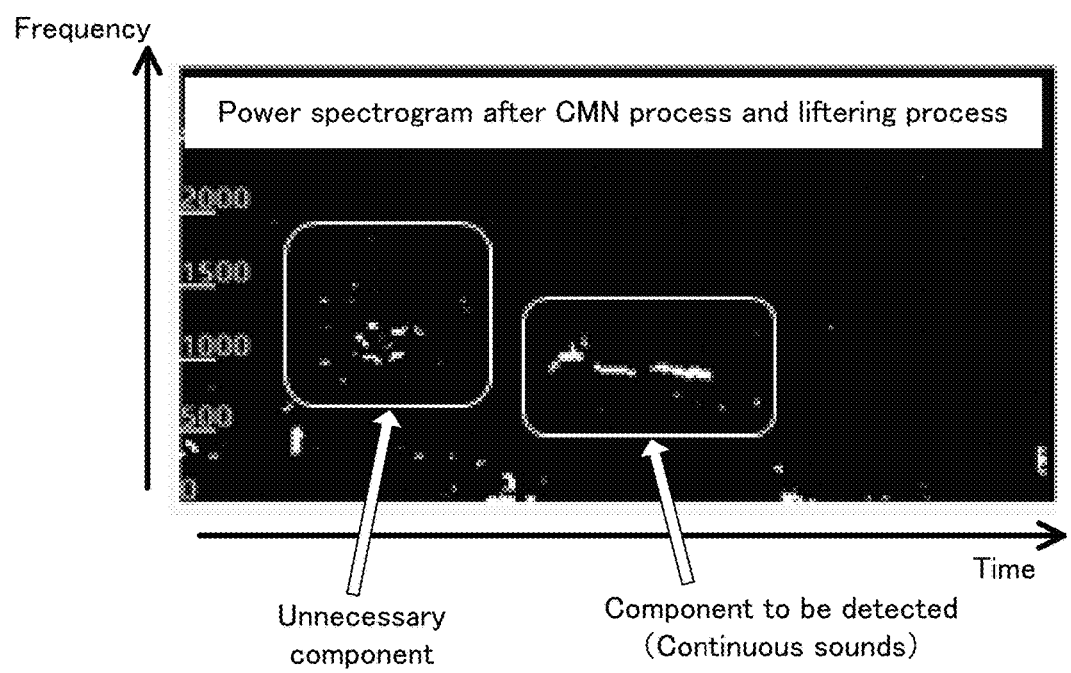
FIG. 18 is a power spectrogram illustrating an example of a power spectrum before an enhancement process using the KL information amount.
Figure 19:
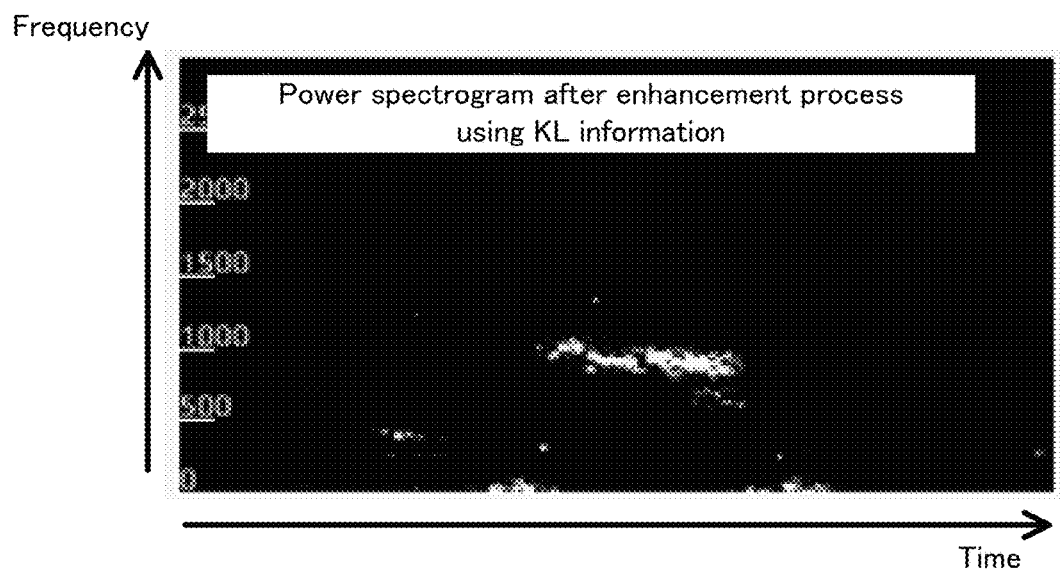
FIG. 19 is a power spectrogram illustrating an example of a power spectrum after the enhancement process using the KL information amount.

Next, a technical effect obtained by the biological sound analyzing apparatus according to the second example explained above will be explained in detail with reference to FIG. 18 and FIG. 19. FIG. 18 is a power spectrogram illustrating an example of a power spectrum before the enhancement process using the KL information amount. FIG. 19 is a power spectrogram illustrating an example of a power spectrum after the enhancement process using the KL information amount.

In FIG. 18, as explained in the first example, the noise included in the breath sound information can be emphasized by performing the CMN process and the liftering process. As in the example illustrated in FIG. 18, however, performing only the CMN process and the liftering process may leave not only a component to be detected, i.e., a continuous sound component, but also an unnecessary component. If the unnecessary component is detected, there is likely an adverse effect in calculating the correlation coefficient.

In contrast, the enhancement process using the KL information amount $D_{KL}$ can further reduce the unnecessary component. In other words, by performing the enhancement process using the KL information amount $D_{KL}$, it is possible to improve detection sensitivity to the continuous sounds, in comparison with when only the CMN process and the liftering process are performed.

In FIG. 19, the unnecessary component, which was left in FIG. 18, is removed in the power spectrogram after the enhancement process using the KL information amount $D_{KL}$. As described above, if the component to be detected is only left, it is possible to calculate a more appropriate correlation coefficient from a result of the enhancement process.

Therefore, according to the biological sound analyzing apparatus in the second example, it is possible to more accurately distinguish the continuous sounds included in the breath sounds.

Third Example

Next, a biological sound analyzing apparatus according to a third example will be explained with reference to FIG. 20 to FIG. 24. The third example is mostly the same as the first and second examples explained above, and is partially different in configuration and operation. Thus, a different part from that of the first example will be explained in detail, and an explanation of the other same part will be omitted, as occasion demands.

Difference from First and Second Examples

The biological sound analyzing apparatus according to the first and second examples is configured to provide a final output, which is whether or not the breath sounds include the continuous sounds. In contrast, the biological sound analyzing apparatus according to the third example is configured to output whether or not the continuous sounds included in the breath sounds are rhonchi.

<Characteristics of Rhonchi and Wheezes>

Figure 20:
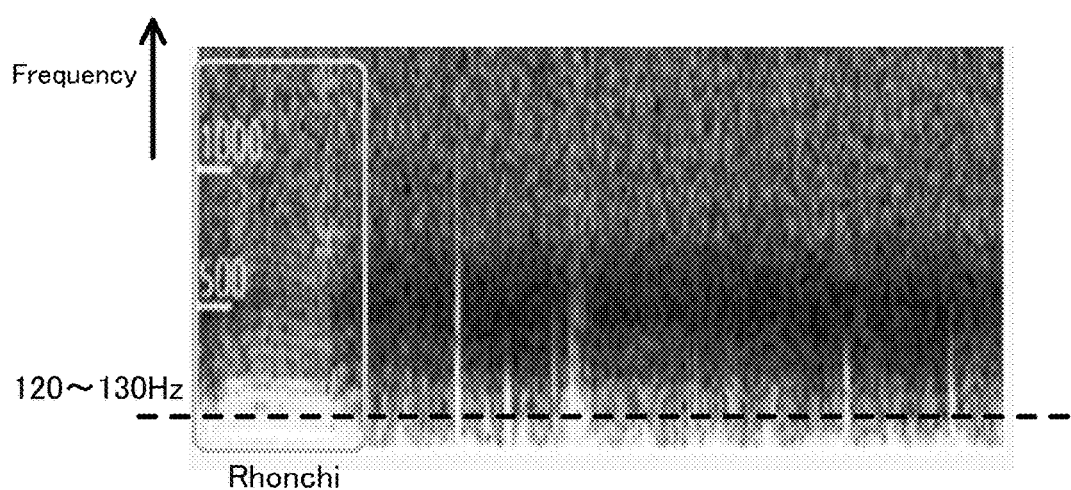
FIG. 20 is a power spectrogram illustrating an example of a power spectrum of biological sounds including rhonchi.
Figure 21:
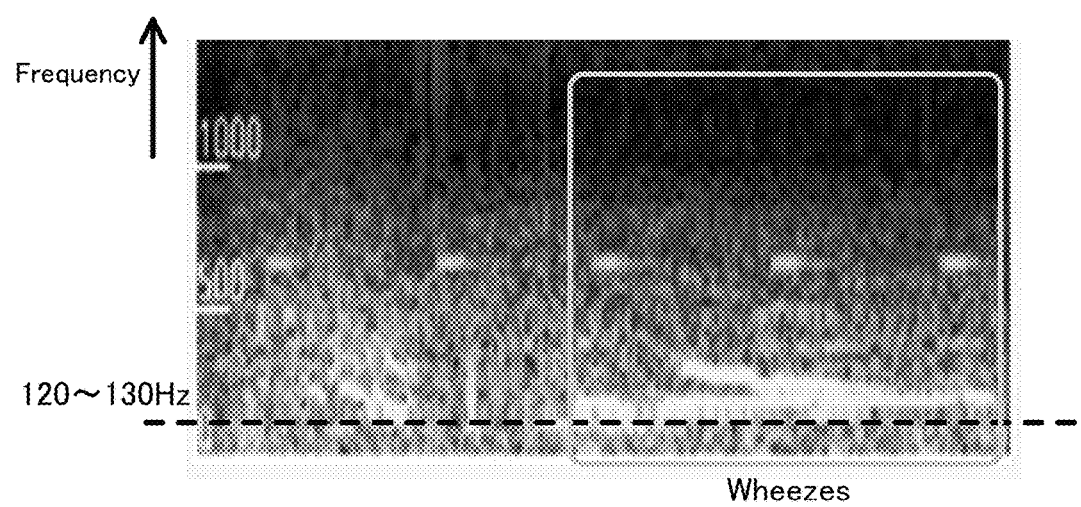
FIG. 21 is a power spectrogram illustrating an example of a power spectrum of biological sounds including wheezes.
Figure 22:
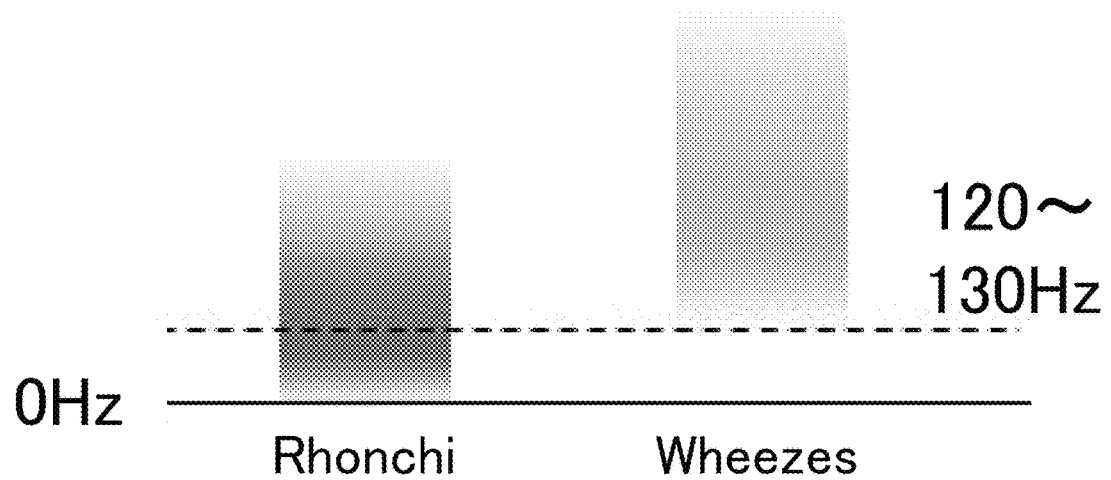
FIG. 22 is a graph illustrating a frequency tendency of rhonchi and wheezes.

Hereinafter, characteristics of rhonchi and wheezes, which are the continuous sounds, will be explained in detail with reference to FIG. 20 to FIG. 22. FIG. 20 is a power spectrogram illustrating an example of a power spectrum of biological sounds including rhonchi. FIG. 21 is a power spectrogram illustrating an example of a power spectrum of biological sounds including wheezes. FIG. 22 is a graph illustrating a frequency tendency of rhonchi and wheezes.

As is clear from a comparison between FIG. 20 and FIG. 21, there is a clear difference between the rhonchi and the wheezes in frequency bands to be generated. Particularly, as observed by using a threshold value of 120 Hz to 130 Hz, the rhonchi are frequently generated even in a part whose frequency is less than or equal to the threshold value, while the wheezes are rarely generated in the part whose frequency is less than or equal to the threshold value. The spectrograms illustrated in FIG. 20 and FIG. 21 are merely an example; however, according to studies by the present inventors, it has been found that the same tendency applies even in the other examples.

As illustrated in FIG. 22, only the rhonchi are included in the part whose frequency is less than or equal to the threshold value of 120 Hz to 130 Hz, and the wheezes are not included. By using this characteristic, it is possible to determine whether the continuous sounds are the rhonchi or the wheezes. In order to appropriately distinguish the rhonchi, it is preferable to use a rhonchi tendency R, which will be explained below.

<Calculation of Rhonchi Tendency>

Figure 23:
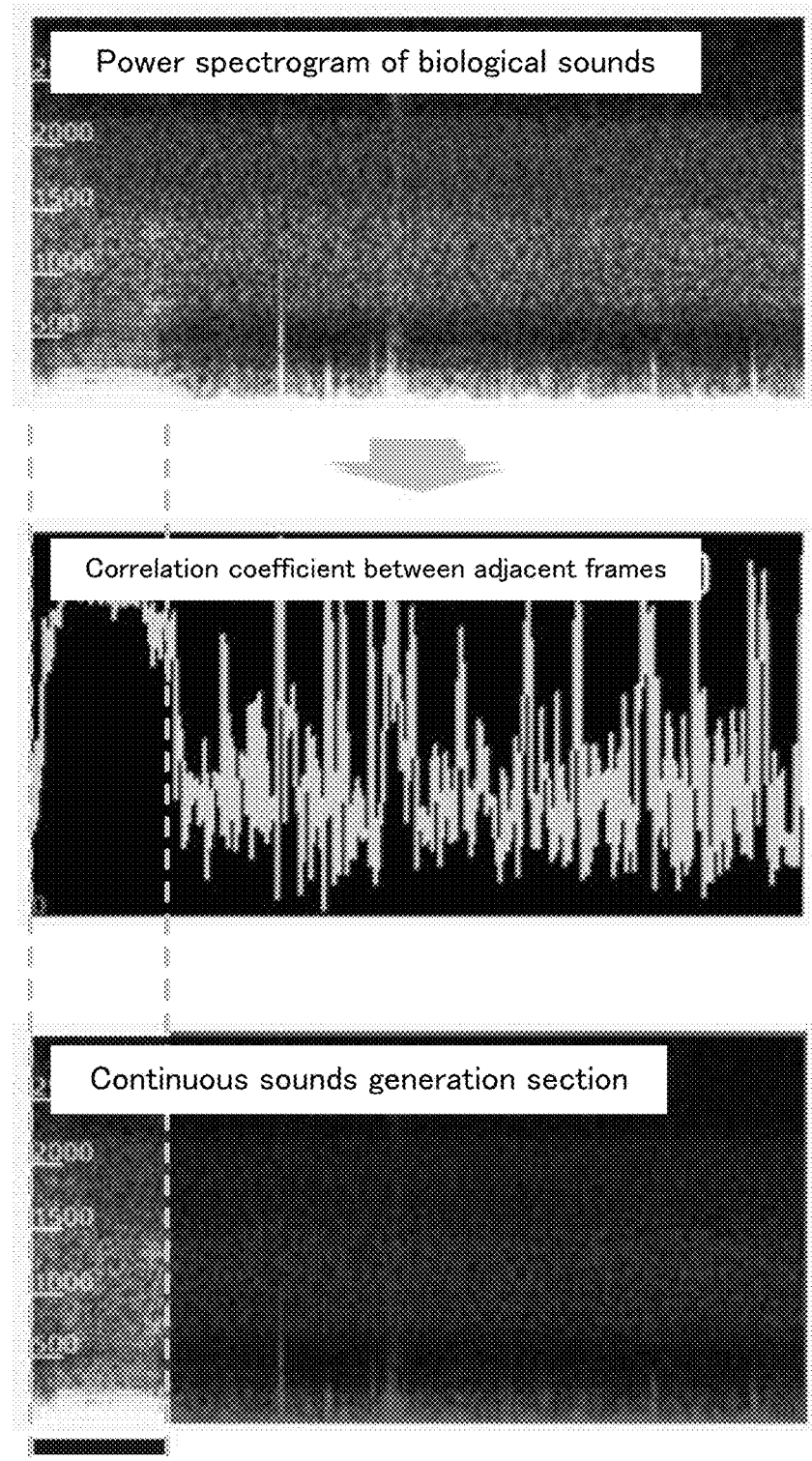
FIG. 23 is a process diagram illustrating a process of calculating a rhonchi tendency of the power spectrogram illustrated in FIG. 20.
Figure 24:
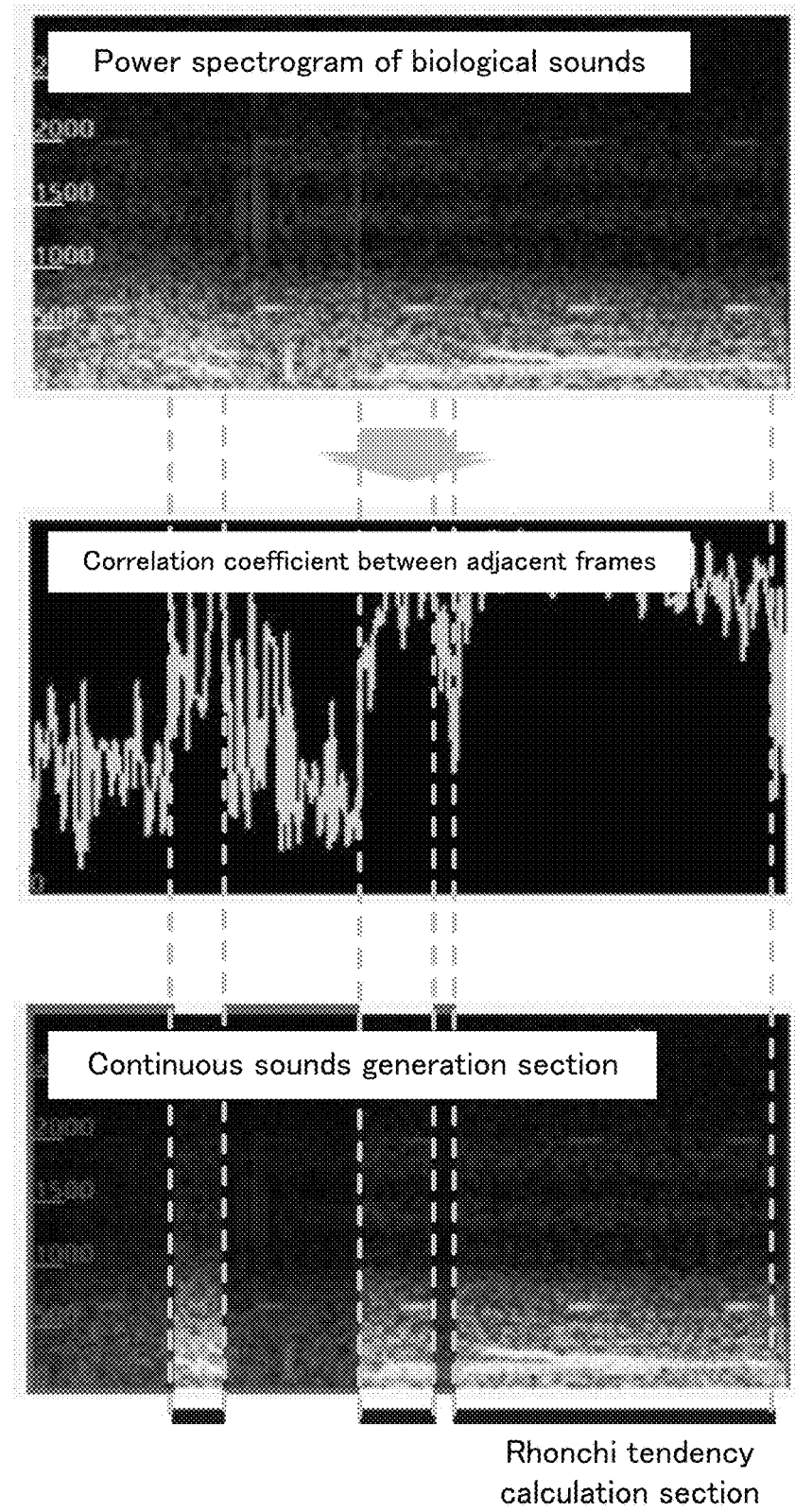
FIG. 24 is a process diagram illustrating a process of calculating the rhonchi tendency of the power spectrogram illustrated in FIG. 21.

A method of calculating the rhonchi tendency R will be explained in detail with reference to FIG. 23 and FIG. 24. FIG. 23 is a process diagram illustrating a process of calculating the rhonchi tendency of the power spectrogram illustrated in FIG. 20. FIG. 24 is a process diagram illustrating a process of calculating the rhonchi tendency of the power spectrogram illustrated in FIG. 21.

As illustrated in FIG. 23 and FIG. 24, in calculating the rhonchi tendency R, a section in which the correlation coefficient P(t) between adjacent frames is greater than or equal to the predetermined threshold value $P_{thre}$ may be detected as a continuous sound generation section. The continuous sound generation section may be detected as a plurality of sections.

Then, a ratio of the power whose frequency is less than or equal to 120 Hz in the continuous sound generation section may be calculated as the rhonchi tendency R. The calculated rhonchi tendency R may be compared with the predetermined threshold value $R_{thre}$. If the rhonchi tendency R is greater than or equal to the predetermined threshold value $R_{thre}$, the continuous sounds may be determined to be the rhonchi. On the other hand, if the rhonchi tendency R is less than the predetermined threshold value $R_{thre}$, the continuous sounds may be determined not to be the rhonchi (e.g., may be determined to be the wheezes).

Effect of Third Example

Lastly, a technical effect obtained by the biological sound analyzing apparatus according to the third example will be explained.

According to the biological sound analyzing apparatus in the third example, it is possible to determine whether or not the continuous sounds are the rhonchi, by using the frequency characteristic of the rhonchi. Particularly, in the third example, the rhonchi tendency R, which is used to determined whether or not the continuous sounds are the rhonchi, may be calculated by using the correlation coefficient P(t). Thus, the temporal continuity is considered, by which a more accurate rhonchi tendency R is calculated.

As described above, according to the biological sound analyzing apparatus in the third example, the continuous sounds included in the breath sounds can be analyzed in more detail and with more accuracy.

The present invention is not limited to the aforementioned embodiments and examples, but various changes may be made, if desired, without departing from the essence or spirit of the invention which can be read from the claims and the entire specification. A biological sound analyzing apparatus, a biological sound analyzing method, a computer program, and a recording medium that involve such changes are also intended to be within the technical scope of the present invention.

DESCRIPTION OF REFERENCE NUMERALS AND LETTERS 100 breath sound acquirer
200 processor
210 time-frequency analyzer
220 cepstrum analyzer
230 noise enhancement processor
240 correlation information calculator
250 continuous sound determinator
300 result display
P(t) correlation coefficient
$C_1$ continuous sound tendency
$D_{KL}$ KL information amount
R rhonchi tendency

The invention claimed is:

1. A biological sound analyzing apparatus comprising:
a sensor configured to obtain first biological sound information, which indicates a change in biological sounds with time;
a processor configured to generate second biological sound information by performing a first process of enhancing first noise information, which indicates noise included in the biological sounds, on the first biological sound information;
a calculator configured to calculate correlation information, which indicates a correlation in adjacent periods of the second biological sound information; and
a display device configured to output second noise information, which indicates continuous noise included in the biological sounds, on the basis of the correlation coefficient.

2. The biological sound analyzing apparatus according to claim 1, wherein the processor is configured to perform a process of reducing a component that is less than or equal to a degree, from cepstrum information, which is calculated by performing an inverse Fourier transform process on the first biological sound information, as the first process.

3. The biological sound analyzing apparatus according to claim 2, wherein the processor is configured to perform a second process of reducing a component that corresponds to a characteristic obtained by averaging a plurality of cepstrum informations in a period, from each of the plurality of cepstrum informations, before performing the first process.

4. The biological sound analyzing apparatus according to claim 3, wherein the processor is configured to calculate an information amount, which is determined in accordance with a deviation amount of the second biological sound information from a reference value, for each section after performing the first process, and said processing device is configured to generate the second biological sound information by performing a third process of reducing a component in which the information amount is less than or equal to a first threshold value.

5. The biological sound analyzing apparatus according to claim 1, wherein said display device is configured to calculate a ratio of a period in which the correlation information continuously exceeds a second threshold value for a time that is greater than or equal to a duration, with respect to a cycle, and said outputting device is configured to output the second noise information if the ratio of the period is greater than or equal to a ratio.

6. The biological sound analyzing apparatus according to claim 1, wherein said display device is configured to output information in which a ratio of a component whose frequency is less than or equal to a frequency is greater than or equal to a third threshold value, out of the second noise information, as third noise information which indicates rhonchi.

7. A biological sound analyzing method comprising:
an obtaining process of obtaining, by a sensor, first biological sound information, which indicates a change in biological sounds with time;
a processing process of generating, by a processor, second biological sound information by performing a first process of enhancing first noise information, which indicates noise included in the biological sounds, on the first biological sound information;
a calculating process of calculating, by the processor, correlation information, which indicates a correlation in adjacent periods of the second biological sound information; and
an outputting process of outputting, by a display, second noise information, which indicates continuous noise included in the biological sounds, on the basis of the correlation coefficient.

8. A non-transitory computer-readable medium having executable instructions executable by a processor, the instructions comprising:
obtaining first biological sound information, which indicates a change in biological sounds with time;
generating second biological sound information by performing a first process of enhancing first noise information, which indicates noise included in the biological sounds, on the first biological sound information;
calculating correlation information, which indicates a correlation in adjacent periods of the second biological sound information; and
outputting second noise information, which indicates continuous noise included in the biological sounds, by using the correlation coefficient to calculate a continuous sound tendency indicative of a characteristic of the continuous noise.

9. The biological sound analyzing apparatus of claim 6, wherein the third noise information indicates rhonchi.

10. The biological sound analyzing method of claim 7, wherein the third noise information indicates rhonchi.

11. The biological sound analyzing method of claim 7, wherein said calculating process comprises calculating a ratio of a period in which the correlation information continuously exceeds a second threshold value for a time that is greater than or equal to a duration, with respect to a cycle, and said outputting process includes outputting the second noise information if the ratio of the period is greater than or equal to a prescribed ratio.

12. The non-transitory computer readable medium of claim 8, wherein said calculating comprises calculating a ratio of a period in which the correlation information continuously exceeds a second threshold value for a time that is greater than or equal to a duration, with respect to a cycle, and said outputting comprises outputting the second noise information if the ratio of the period is greater than or equal to a prescribed ratio.

13. The non-transitory computer readable medium of claim 8, wherein said outputting includes outputting information in which a ratio of a component whose frequency is less than or equal to a frequency is greater than or equal to a third threshold value, out of the second noise information, as third noise information.

14. The non-transitory computer readable medium of claim 13, wherein the third noise information indicates rhonchi.

15. The non-transitory computer readable medium of claim 8, wherein the obtaining comprises cepstral mean normalization (CMN) and liftering to cut a low-degree quefrency component of a cepstrum, to enhance the first biological sound information.

16. The non-transitory computer readable medium of claim 15, further comprising calculating a parameter based on an observation value and a power distribution subjected to the CMN and the liftering, comparing the parameter to a reference value, and based on a result of the comparing, cutting a component of the first biological sound information to enhance the first biological sound information.

17. The non-transitory computer readable medium of claim 8, wherein the continuous sound tendency is calculated as a ratio of a period in which a correlation coefficient continuously exceeds a threshold value for a time greater than or equal to a duration, and for the correlation coefficient exceeding the threshold value, determining that the continuous noise is associated with one or more breath sounds.

* * * * *